United States Patent
Ferdinandy et al.

(10) Patent No.: US 9,487,462 B2
(45) Date of Patent: Nov. 8, 2016

(54) INHIBITORS OF MATRIX METALLOPROTEINASES

(75) Inventors: Péter Ferdinandy, Szeged (HU); Tamás Bálint Csont, Szeged (HU); Csaba Csonka, Szeged (HU); Krisztina Kedvesné Kupai, Szeged (HU); László Kovács, Budapest (HU); Attila Kis-Tamás, Budapest (HU); Ferenc Tamás Takács, Monor (HU); Dénes Kónya, Budapest (HU); Gábor Medgyes, Budapest (HU); Sándor Cseh, Dunakeszi (HU); István Hajdú, Budapest (HU); Zsolt Lörincz, Budapest (HU); György Dormán, Budapest (HU); Anikó Görbe, Szeged (HU)

(73) Assignees: PharmaHungary 2000 Kft., Szeged (HU); TargetEx Kft., Dunakeszi (HU)

( * ) Notice: Subject to any disclaimer, the term of this patent is extended or adjusted under 35 U.S.C. 154(b) by 411 days.

(21) Appl. No.: 13/990,684

(22) PCT Filed: Dec. 19, 2011

(86) PCT No.: PCT/HU2011/000127
§ 371 (c)(1),
(2), (4) Date: Aug. 1, 2013

(87) PCT Pub. No.: WO2012/080762
PCT Pub. Date: Jun. 21, 2012

(65) Prior Publication Data
US 2013/0303572 A1 Nov. 14, 2013

(30) Foreign Application Priority Data
Dec. 17, 2010 (HU) .................... 1000676

(51) Int. Cl.
| | | |
|---|---|---|
| A61K 31/4025 | (2006.01) |
| A61K 31/417 | (2006.01) |
| C07C 47/575 | (2006.01) |
| C07D 213/30 | (2006.01) |
| C07D 233/64 | (2006.01) |
| C07D 233/90 | (2006.01) |
| C07D 277/28 | (2006.01) |
| C07D 277/56 | (2006.01) |
| C07D 401/12 | (2006.01) |
| C07D 417/12 | (2006.01) |
| C07D 417/14 | (2006.01) |
| C07D 213/38 | (2006.01) |
| C07D 277/30 | (2006.01) |
| C07D 295/16 | (2006.01) |

(52) U.S. Cl.
CPC ........... *C07C 47/575* (2013.01); *C07D 213/30* (2013.01); *C07D 213/38* (2013.01); *C07D 233/64* (2013.01); *C07D 233/90* (2013.01); *C07D 277/28* (2013.01); *C07D 277/30* (2013.01); *C07D 277/56* (2013.01); *C07D 295/16* (2013.01); *C07D 401/12* (2013.01); *C07D 417/12* (2013.01); *C07D 417/14* (2013.01)

(58) Field of Classification Search
CPC ........................ A61K 31/4025; A61K 31/417
USPC ................ 514/241, 252.01, 252.1, 256, 319
See application file for complete search history.

(56) References Cited

U.S. PATENT DOCUMENTS

| 4,125,530 A | 11/1978 | Baldwin et al. |
| 5,716,929 A | 2/1998 | Bemis et al. |

(Continued)

FOREIGN PATENT DOCUMENTS

| WO | 96/15096 | 5/1996 |
| WO | 2004/094395 A2 | 11/2004 |

(Continued)

OTHER PUBLICATIONS

Heindel et al.: "Imidazole Carboxylates by a Claisen-Type Rearrangement of Amidoxime-Propiolate Adducts", Tetrahedron Letters, 1971, No. 18, pp. 1439-1440.

(Continued)

*Primary Examiner* — San-Ming Hui
(74) *Attorney, Agent, or Firm* — Jason D. Voight

(57) ABSTRACT

Compounds of general formula (I), salts or solvates thereof and pharmaceutical compositions containing same:

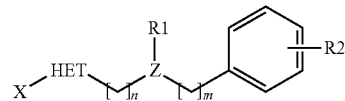

wherein Z is N or CH or the Z(R1) part is replaced with a covalent bond, m and n is 0, 1, 2 or 3; HET is heteroaryl; X is $CF_3$, halogen, CO-heterocyclyl, COOR3 or CONHR3; R1 is H, $(CH_2)_o$-aryl, $(CH_2)_p$-heteroaryl, $(CH_2)_q$-biphenyl; C(O)—R5; $S(O)_2$—R6; R2 is H, aryl, heteroaryl, Y—$(CH_2)_r$-aryl, Y—$(CH_2)_s$-heteroaryl, where some of the above substituents may be substituted; Y is O or S; with the exclusion of the compound where HET is 1,3-thiazol, X is COOH, R1 is 4-fluorophenyl and R2 is benzyloxy. The invention also relates to the use of a compound of general formula (I), salts or solvates thereof for the use in the prevention or treatment of diseases where the activation of MMPs is involved in the pathomechanism. In this aspect the use of the above excluded compound is also inventive.

14 Claims, 6 Drawing Sheets

(56) References Cited

U.S. PATENT DOCUMENTS

| | | |
|---|---|---|
| 2005/0054626 A1 | 3/2005 | Carter et al. |
| 2006/0089364 A1 | 4/2006 | Capet et al. |
| 2008/0287506 A1* | 11/2008 | Roush .................. A01N 43/36 514/343 |
| 2010/0105894 A1 | 4/2010 | Inaba et al. |
| 2012/0184521 A1 | 7/2012 | Kawaminami et al. |

FOREIGN PATENT DOCUMENTS

| | | |
|---|---|---|
| WO | 2006/078942 A2 | 7/2006 |
| WO | 2007/117981 A2 | 10/2007 |
| WO | 2008/079277 A1 | 7/2008 |
| WO | 2009/140101 A2 | 11/2009 |
| WO | 2011/003191 A1 | 1/2011 |
| WO | 2011/037192 A1 | 3/2011 |

OTHER PUBLICATIONS

Breslow et al.: "Synthesis of Some Polyimidazole Ligands Related to Zinc Enzymes", J. Am. Chem. Soc., 1983, vol. 105, pp. 5337-5342.

Baldwin et al.: "4-Trifluoromethylimidazoles and 5-(4-Pyridyl)-1,2,4-triazoles, New Classes of Xanthine Oxidase Inhibitors", Journal of Medicinal Chemistry, 1975, vol. 18, No. 9, pp. 895-900.

Chapman et al.: "Synthesis of Some 5-Substituted Benzo[b]thiophens Related to Gramine", Journal of the Chemical Society, 1965, p. 774.

Potter et al.: "Discovery of cell-active phenyl-imidazole Pin1 inhibitors by structure-guided fragment evolution", Bioorganic & Medicinal Chemistry Letters, 2010, vol. 20, pp. 6483-6488.

Haemmerle et al.: "Comparing the Reactivity of the 4- and 5-Positions of 2-Phenylthiazoles in Stille Cross-Coupling Reactions", SYNLETT, 2007, No. 19, pp. 2975-2978.

* cited by examiner

INHIBITORS OF MATRIX METALLOPROTEINASES

This is the national stage of International Application PCT/HU2011/000127, filed Dec. 19, 2011.

FIELD OF THE INVENTION

The present invention relates to the use of therapeutically active novel matrix metalloproteinase (MMP) inhibitor compounds having anti-ischemic and cytoprotective effect, and to use of them for preventing and treating cardiac and non-cardiac diseases, where activation of MMPs is involved in the pathomechanism.

BACKGROUND OF THE INVENTION

MMPs are a family of zinc-dependent enzymes comprised of more than 25 individual members divided into specific classes based on in vitro substrate specificity for various ECM components. The most important ones are given in Table I.

TABLE I

| MMP superfamily | | | |
|---|---|---|---|
| Group | MMP | Name | Size (kD) |
| Collagenase | 1 | Interstitial collagenase | 52/55 |
| | 8 | Neutrophil collagenase | 75 |
| | 13 | Collagenase-3 | 54 |
| Gelatinase | 2 | Gelatinase A | 72 |
| | 9 | Gelatinase B | 92 |
| Stromelysin | 3 | Stromelysin-1 | 52/58 |
| | 7 | Matrilysin | 28 |
| | 10 | Stromelysin-2 | 58 |
| | 11 | Stromelysin-3 | 29 |
| Elastase | 12 | Metalloelastase | 53 |
| Membrane type | 14 | MT1-MMP | 66 |
| | 15 | MT2-MMP | 76 |
| | 16 | MT3-MMP | 70 |
| | 17 | MT4-MMP | 53 |
| | 24 | MT5-MMP | 63 |
| | 25 | MT6-MMP | 65 |

The table was imported from Lindsey, 2004.

Timely degradation of extracellular matrix (ECM) is an important feature of development, morphogenesis, tissue repair and remodelling. It is precisely regulated under normal physiological conditions, but when dysregulated it becomes a cause of many diseases such as arthritis, nephritis, cancer, encephalomyelitis, chronic ulcers, fibrosis etc. Uncontrolled ECM remodelling of the myocardium and vasculature are features of cardiovascular disorders such as atherosclerosis, stenosis, left ventricular hypertrophy, heart failure and aneurysm. MMP roles in normal and pathophysiological processes have been demonstrated and a partial list of diseases is provided in Table II.

TABLE II

| The role of MMPs in different pathologies | | | |
|---|---|---|---|
| Type of MMP | Disease | Source | References |
| MMP-1 | Atherosclerosis, Melanoma, Heart failure | Human | (Lehrke et al., 2009); |
| MMP-2 | Heart failure, Gastritis, Rheumatoid arthritis | Human | (Lin et al., 2009); (Yoshida et al., 2009) |
| MMP-3 | Brain injury, Neurodegenaration | Human, Rat | (Grossetete et al., 2009); (McClain et al., 2009) |
| MMP-7 | Tumor-induced osteolysis, Colon cancer | Mice, HT29 cells | (Thiolloy et al., 2009); (Fang et al., 2009) |
| MMP-8 | Coronary artery disease, Angina | Human | (Shah et al., 2009); (Momiyama et al., 2009) |
| MMP-9 | Myocarditis and subsequent dilated cardiomyopathy | Rat | (Matsumoto et al., 2009) |
| MMP-10 | Marfan's syndrome, Lung cancer | Human | (Do & Nataatmadja) 2007); (Zhang et al., 2007) |
| MMP-11 | Tumor progression, Breast carcinomas | Human | (Matziari et al., 2007); (Selvey et al., 2004) |
| MMP-12 | Granulomatous skin diseases, Inflammatory disorders | Human | (Vaalamo et al., 1999); (Lagente et al., 2009) |
| MMP-13 | Breast carcinomas | Human | (Zhang et al., 2008); |
| Membrane - type MMPs | Tumor growth by activating MMP-2 | Human Rat | (Lang et al., 2004); (Davis & Saunders, 2006); (Hernandez-Barrantes et al., 2002) |
| MMP-19 | Rheumatoid arthritis | Human | (Sedlacek et al., 1998); |
| MMP-20 | Amelogenesis imperfecta | Human | (Stephanopoulos et al., 2005) |
| MMP-21 | Melanoma, ovarian and Colon carcinomas | Human | (Kuivanen et al., 2005); (Ahokas et al., 2002) |
| MMP-22 | No data available | | |
| MMP-23 | Breast cancer | Human | (Hegedus et al., 2008) |
| MMP-24 | Brain tumors | Human | (Llano et al., 1999) |
| MMP-25 | Inflammatory hyperalgesia | Mice | (Folgueras et al., 2009) |
| MMP-26 | Lung cancer | Human | (Li et al., 2009) |

The table was imported from (Kupai et al., 2010).

MMPs in the Heart

In normal hearts, MMPs are present predominantly as so-called pro-MMPs and are often co-expressed in a complex with their endogenous inhibitors, the tissue inhibitors of metalloproteinases (TIMPs) (Woessner, Jr., 2002). In the heart, MMP-2 is ubiquitously expressed and found in normal cardiac myocytes as well as endothelium, vascular smooth muscle cells and fibroblasts (Spinale, 2007; Schulz, 2007). There is an ever-growing list of pathological roles of MMPs in cardiovascular diseases, including atherosclerosis, angioplasty, restenosis and ischemic heart disease, as well as heart failure (Spinale, 2007; Matsumoto et al., 2009; Kitaoka et al., 2010). It has been showed that pharmacological inhibition of MMPs produces cardioprotection in both normal and hyperlipidemic rats and found that myocardial ischemic adaptation attenuates nitrosative stress and the activation of MMPs in rat hearts (Giricz et al., 2006; Kitaoka et al., 2010; Csonka et al., 2001). Moreover acute treatment with MMP inhibitor (MMPI) is able to attenuate ischemia reperfusion injury and decrease myocardial infarct size and acute heart failure induced by pro-inflammatory cytokines in rats (Gao et al., 2003). In addition, MMPs have been shown to target several non-extracellular matrix proteins both inside and outside the cells some of which is an important member of acute endogenous tissue protective pathways (Sung et al., 2007). Consequently, MMPs became potential targets to combat not only chronic infarction and heart failure, but also acute cardiovascular diseases such as acute myocardial ion or systemic inflammation-induced acute heart failure.

Close to 60 matrix metalloproteinase inhibitors have been pursued as clinical candidates in the last 3 decades targeting indications such as cancer, arthritis, cardiovascular diseases and many others (Fingleton, 2007). However, the clinical development of all the MMP inhibitors (except doxycycline for periodontal disease) have been discontinued due to safety reasons and lack of efficacy. The application of MMP inhibitors targeting acute cardiovascular diseases has not reached the clinical phase yet. As most of the side effects of MMPIs occurred during chronic treatment, acute application of MMP inhibitors especially selective MMP-2 and MMP-9 inhibitors may give confidence towards a successful clinical trial targeting acute cardiovascular diseases (Dorman et al., 2010; Dorman et al., 2007).

Acute Actions and Novel Targets of Matrix Metalloproteinases

There is emerging evidence implicating the acute actions of MMP proteolytic activity in the pathogenesis of vascular diseases such as septic shock, pre-eclampsia and ischemia/reperfusion injury. This field of research represents a new frontier in MMP biology. MMP-2 is able to proteolytically cleave Troponin I in hearts subjected to ischemia and reperfusion injury (Wang et al., 2002). Troponin I and myosin light chain-1 are among a growing list of newly discovered substrates of MMP-2 unrelated to the extracellular matrix, each invoking a novel biological action of this MMP (Polewicz et al., 2010). These substrates include big-endothelin (Fernandez-Patron et al., 1999), calcitonin-gene-related peptide (Fernandez-Patron et al., 2000a), and monocyte chemoattractant protein-3 (Fernandez-Patron et al., 2000b). MMP-2 was also shown to mediate neurotoxicity in HIV-infected macrophages by cleavage of the chemokine stromal cell-derived factor-1 to a cleavage product that is neurotoxic (Zhang et al., 2003). Thus the term "matrix metalloproteinase" does not properly reflect the full spectrum of biological activities of these proteases.

Metylamino-Azol-Carboxylic Acid Derivatives as MMP Inhibitors

WO96/15096 describes a tricyclic compound family containing carboxylic acid warhead used in a method of treating a human to achieve an effect, wherein the effect is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control; the method comprising administering an amount of the tricyclic compound, which is effective to inhibit the activity of at least one matrix metalloprotease in said human, thereby to achieve said effect.

There are 2 possibly closest structures in patent WO96/15096 which is in relation with ours:

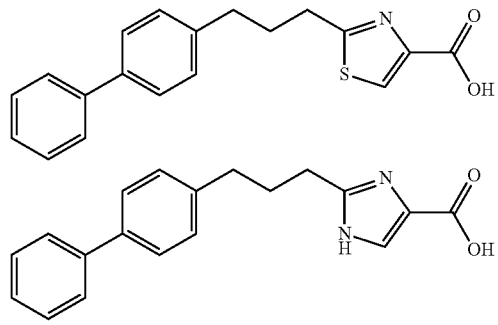

WO2007117981 describes a novel compound library of structure of N-sulphonylated alpha acid hydroxamate, which is inhibitor of MMP-9, and/or MMP-12 and/or MMP-13, and thus can be employed for the treatment of a disorder or disease characterized by abnormal activity of MMP-9 and/or MMP-12 and/or MMP-13. Accordingly, the N-amino-sulphonylated alpha amino acid hydroxamate compound can be used in treatment of disorders or diseases mediated by MMP-9 and/or MMP-12 and/or MMP-13 and the invention also provides a pharmaceutical composition.

The invention described in US 2010105894 relates to a novel cyclopropane compound. In further detail, the present invention relates to a cyclopropane compound or a pharmaceutically acceptable salt thereof having an aggrecanase inhibitory activity or matrix metalloproteinase (MMP) inhibitory activity, a pharmaceutical composition which comprises this compound and a pharmaceutical use thereof.

WO 2009140101 discloses imidazopyridine compounds useful as MMP-13 inhibitors. The invention discloses synthesis and application of imidazo[1,2-a]pyridine-2,5-dicarboxamide derivatives suitable for treating rheumatoid arthritis, osteoarthritis, osteoporosis, peridontosis, artherosclerosis, congestive heart failure, multiple sclerosis or tumor metastasis.

There's a screening compound which is commercialized by AMRI, Albany, N.Y., USA (product code: (ALBH-03203562) and which structure falls into the scope of claim of this patent: 2-[({[4-(benzyloxy)phenyl]methyl}[(4-fluorophenyl)methyl]amino)methyl]-1,3-thiazole-4-carboxylic acid. The compound was sold as screening compound only, without the indication of any biological activity on whatever type of biological substance.

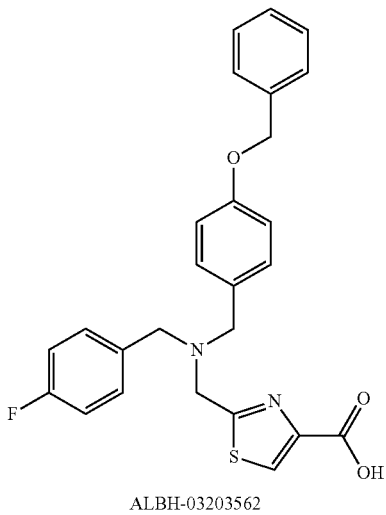 [SMILES: O=C(O)c1csc(CN(Cc2ccc(F)cc2)Cc2ccc(OCc3ccccc3)cc2)n1]

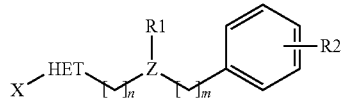

This compound is excluded from the claim relating to new compounds, but involved in the use and pharmaceutical compositions claims. It is given in as "ALBH-known".

SUMMARY OF THE INVENTION

The present invention relates to compounds of general formula (I), salts and solvates thereof:

$$X\text{---}HET\underset{n}{\text{---}}\overset{R1}{\underset{|}{Z}}\underset{m}{\text{---}}\text{Ph}\text{---}R2$$

wherein
Z is N or CH or the Z(R1) part is replaced with a covalent bond,
n is 0, 1, 2 or 3
m is 0, 1, 2 or 3,
HET is heteroaryl;
X is $CF_3$, halogen, CO-heterocyclyl, COOR3 or CONHR3, wherein R3 is H or $C_{1-6}$ alkyl;
R1 is H, $(CH_2)_o$-aryl, $(CH_2)_p$-heteroaryl, $(CH_2)_q$-biphenyl, wherein o, p and q is 1, 2 or 3, or $C_{1-6}$ alkyl which is optionally substituted with 1 or 2 aryl group(s), or R1 is absent when Z is a valence bond;
C(O)—R5, where R5 is H, $C_{1-6}$ alkyl, cycloalkyl, aryl or heteroaryl;
$S(O)_2$—R6, where R6 is H, $C_{1-6}$ alkyl, cycloalkyl aryl or heteroaryl;
R2 is H, aryl, heteroaryl, Y—$(CH_2)_r$-aryl, Y—$(CH_2)_s$-heteroaryl, wherein r and s is 1, 2 or 3, or Y—($C_{1-6}$ alkyl) which is optionally substituted with 1 or 2 aryl group(s);
Y is O or S;
wherein each instance of alkyl is optionally substituted with 1-3 substituent(s) independently selected from the group of halogen, alkoxy, hydroxyl, carboxyl, $CF_3$, nitro, sulphate, amino, monoalkylamino, dialkylamino and cyano;
wherein each instance of cycloalkyl, heterocycloalkyl, aryl, heteroaryl and biphenyl is optionally substituted with 1-3 substituent(s) independently selected from the group of halogen, alkyl, alkoxy, hydroxyl, carboxyl, $CF_3$, nitro, sulphate, amino, monoalkylamino, dialkylamino and cyano;
with the exclusion of the compound where HET is 1,3-thiazol, X is COOH, R1 is 4-fluorophenyl and R2 is benzyloxy.

The above compounds and compositions have MMP inhibitor activity, especially MMP-2, MMP-9 and MMP-13 inhibitor activity, anti-ischemic and cytoprotective effects.

Another aspect of the invention is the use of compounds of formula (I) for the prevention and/or treatment of cardiac and non-cardiac diseases, where activation of MMPs are involved in the pathomechanism. The compounds of formula (I) have a cytoprotective effect which is especially useful in the prevention and/or treatment of the mentioned diseases.

Another aspect of the invention is the use of compounds of formula (I) in the prevention and/or treatment of cardiac and non-cardiac diseases, where activation of MMPs are involved in the pathomechanism.

The invention also relates to pharmaceutically acceptable salts or solvates of compound of general formula (I).

The invention also relates to pharmaceutical composition comprising at least one compound of general formula (I) together with one or more usual pharmaceutical auxiliary material(s).

In case of the above uses and the pharmaceutical composition the scope of compounds includes the ALBH-known compound, too (since no pharmaceutical effect was disclosed for that), i.e. the compound where HET is 1,3-thiazol, X is COOH, R1 is 4-fluorophenyl and R2 is benzyloxy is not excluded from the scope in case of these inventions.

In a preferred embodiment the compound of formula (I) has a carboxylic acid warhead combined with certain thiazole ring structures because these type of compounds have outstanding MMP inhibitor activity. As the structure activity relationship of the thiazole ring system was further investigated, it was realized that a related imidazole ring based structure has an opportunity of wider chemical parameter set, better bioavailability and selectivity, so these subfamily is also regarded as a preferred embodiment.

DETAILED DESCRIPTION OF THE INVENTION

Figure 1:
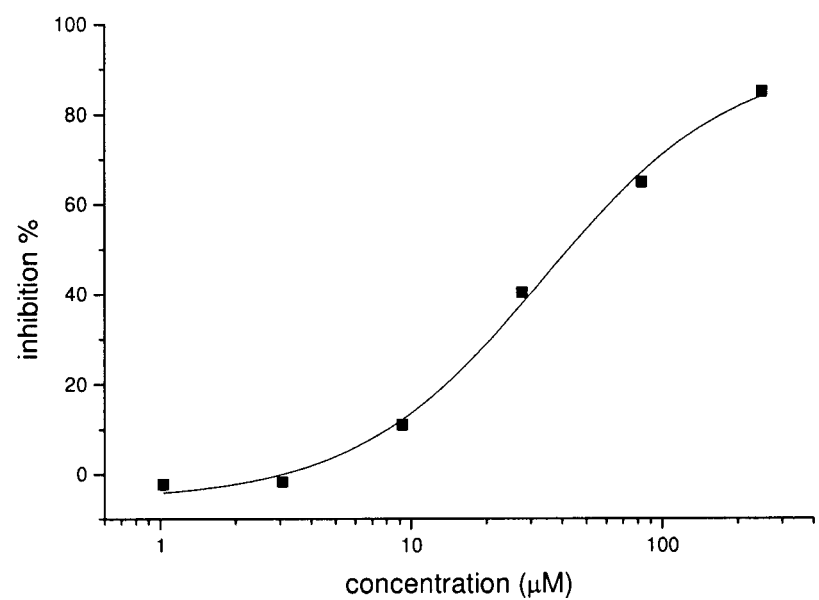
FIG. 1. Dose response curve of Example 1. ($IC_{50}$=46 μM, top panel) and ilomastat on MMP1 inhibition ($IC_{50}$=0.5 nM, bottom panel)
Figure 1:
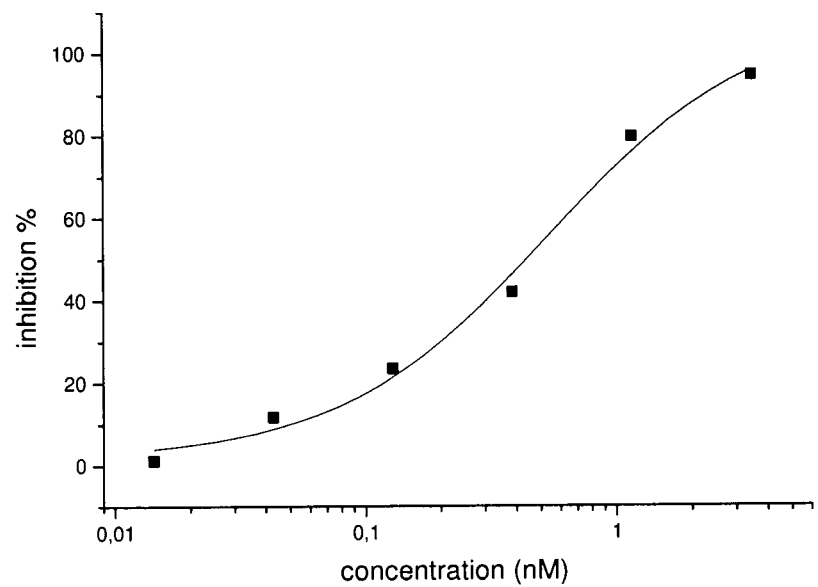
Figure 2:
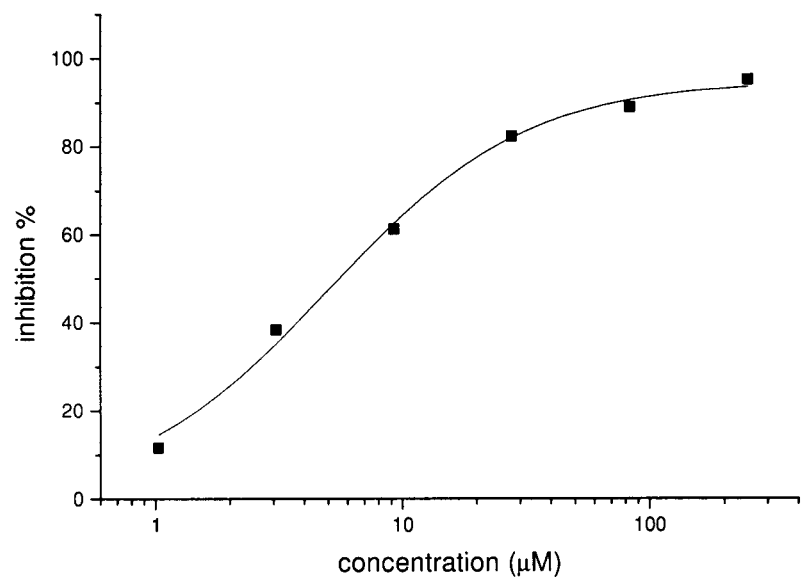
FIG. 2. Dose response curve of Example 1. ($IC_{50}$=5.7 μM, top panel) and ilomastat on MMP2 inhibition ($IC_{50}$=1.0 nM, bottom panel)
Figure 2:
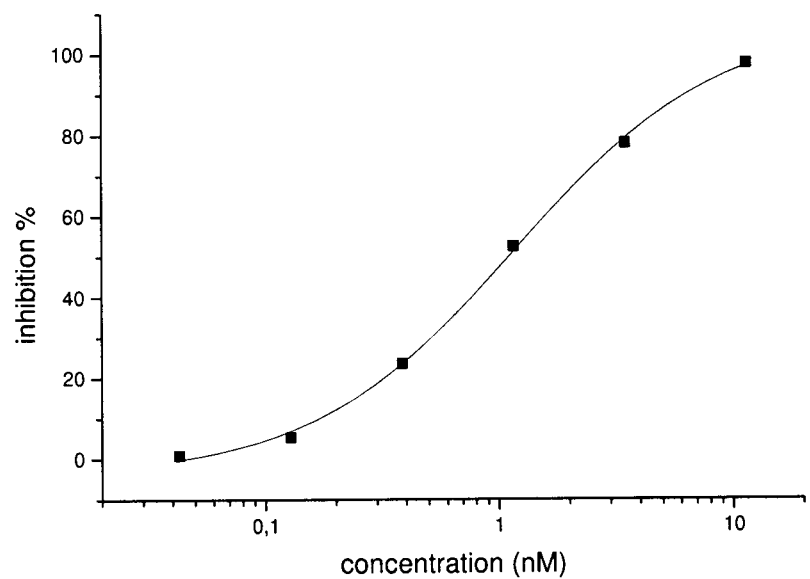
Figure 3:
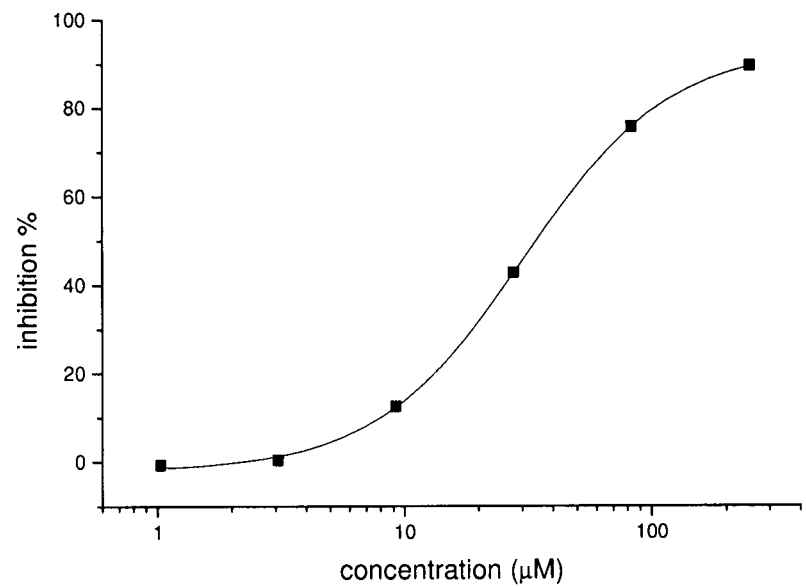
FIG. 3. Dose response curve of Example 1 ($IC_{50}$=31 μM, top panel) and ilomastat on MMP9 inhibition ($IC_{50}$=0.1 nM, bottom panel)
Figure 3:
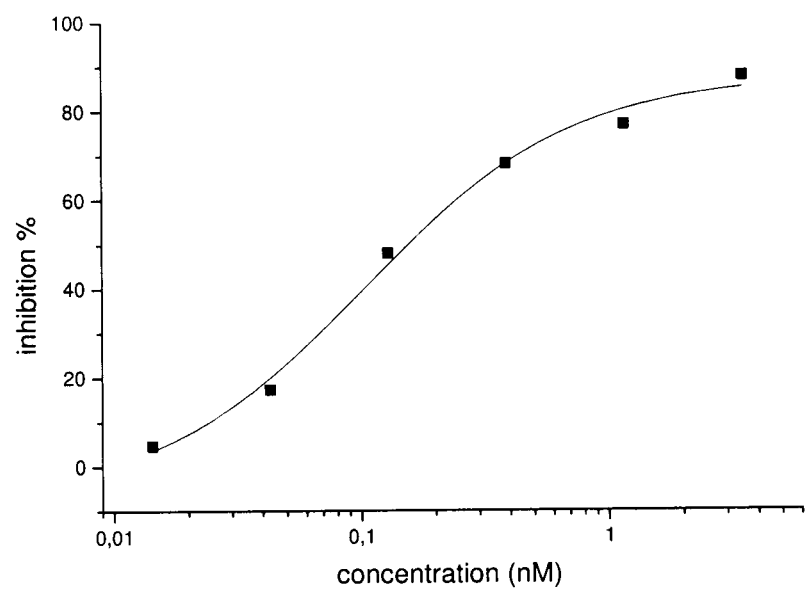
Figure 4:
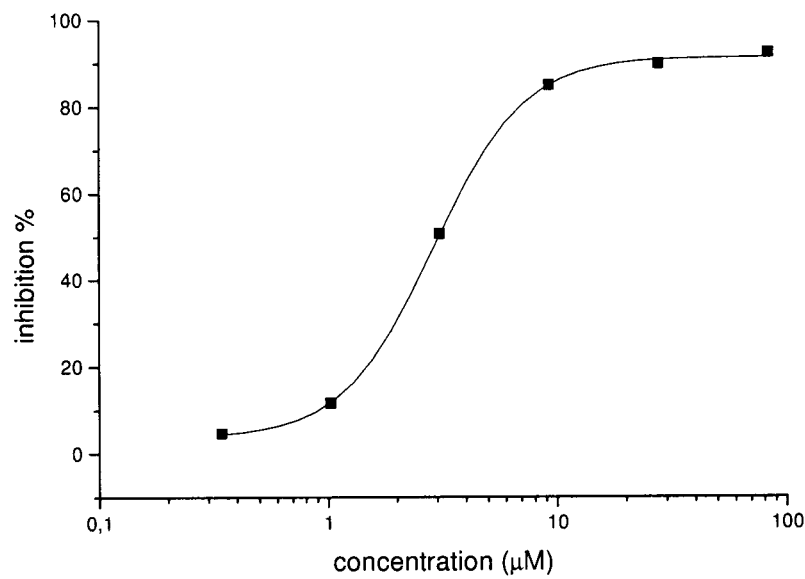
FIG. 4. Dose response curve of Example 1. ($IC_{50}$=2.5 μM, top panel) and ilomastat on MMP13 inhibition ($IC_{50}$=0.2 nM, bottom panel)
Figure 4:
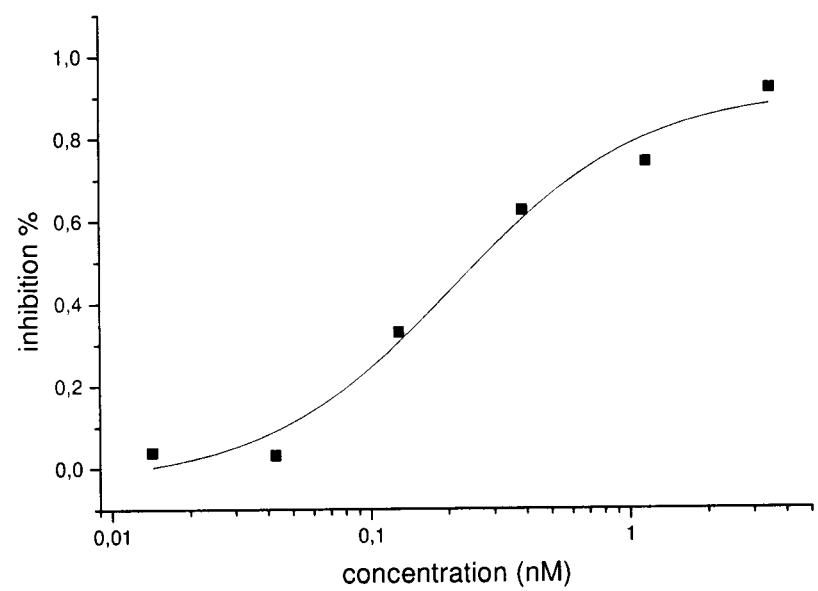
Figure 5:
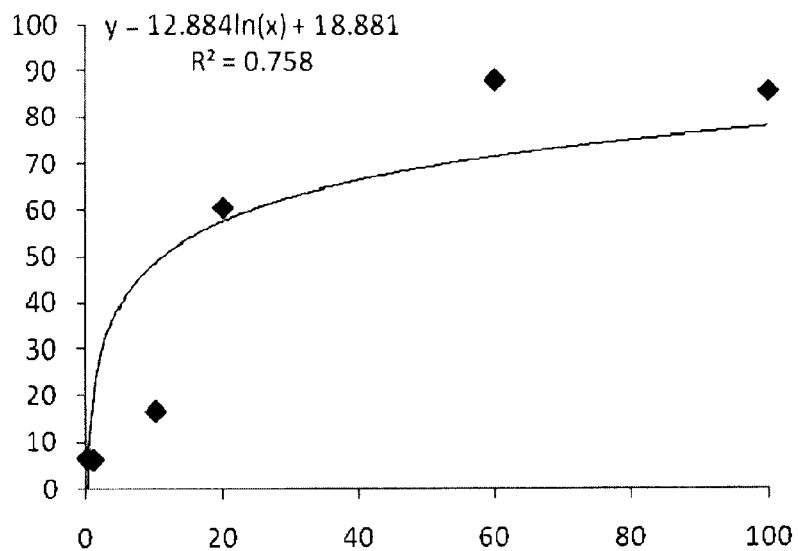
FIG. 5. Representative dose response curve of Compound 1 inhibitor on MMP-2 enzyme.

As it is used herein, the term "aryl", alone or in combinations means an aromatic monocyclic or multicyclic ring system comprising 6 to about 14 carbon atoms, preferably 6 to about 10 carbon atoms. Non-limiting examples of suitable aryl groups include phenyl and naphthyl, where phenyl is a preferred embodiment.

In case of aryl groups the "optionally substituted" means that the group may carry one or more substituent(s) usually applied in the organic chemistry for substitution of aryl groups. So, the substituted aryl groups carry one or more, e.g. 1 to 3, preferably 1 or 2 substituent(s), independently selected from the group of halogen, alkyl, alkoxy, hydroxyl, carboxyl, $CF_3$, nitro, sulphate, amino, monoalkylamino, dialkylamino and cyano (halogen, $CF_3$, alkyl and alkoxy are preferred ones). However, in some preferred compound aryl has no substituent.

In a preferred embodiment the aryl group is phenyl, which is optionally substituted with halogen (i.e. it is a haloaryl group), more preferably F, Cl, Br substituted phenyl, most preferably 4-F-Ph.

As it is used herein, the term "heteroaryl" means a single ring, bicyclic or benzofused heteroaromatic group of 5 to 10 atoms comprising 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidinyl, pyridazinyl and triazolyl. Examples of bicyclic heteroaryl groups are naphthyridyl (e.g., 1.5 or 1.7), imidazopyridyl, pyridopyrimidinyl and 7-azaindolyl. Examples of benzofused heteroaryl groups are indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl.

In case of heteroaryl groups the "optionally substituted" means that the group may carry one or more substituent(s) usually applied in the organic chemistry for substitution of heteroaryl groups. So, the substituted heteroaryl groups carry one or more, e.g. 1 to 3, preferably 1 or 2 substituent(s), independently selected from the group of halogen, alkyl, alkoxy, hydroxyl, carboxyl, $CF_3$, nitro, sulphate, amino, monoalkylamino, dialkylamino and cyano (halogen, $CF_3$, alkyl and alkoxy are preferred ones). However, in some preferred compound heteroaryl has no substituent.

When the heteroaryl group is a benzofused ring, the substituents can be attached to either or both the phenyl ring portion and the heteroaromatic ring portion, and the heteroaryl group can be attached to the rest of the molecule either through the phenyl ring portion or the heteroaromatic ring portion.

As it is used herein, the term "alkyl" alone or in combinations means a straight or branched-chain alkyl group containing from 1 to 7, preferably 1 to 6 carbon atom(s), more preferably 1 to 4 carbon atom(s) such as methyl, ethyl, propyl, isopropyl, butyl, sec-butyl, t-butyl and pentyl. The abbreviation "$C_{x-y}$alkyl" relates to an alkyl having X to Y carbon atom(s).

In case of alkyl groups the "optionally substituted" means that the group may carry one or more substituent(s) usually applied in the organic chemistry for substitution of alkyl groups. So, the substituted alkyl groups carry one or more, e.g. 1 to 3, preferably 1 or 2 substituent(s), independently selected from the group of halogen, alkoxy, hydroxyl, carboxyl, $CF_3$, nitro, sulphate, amino, monoalkylamino, dialkylamino and cyano (halogen, $CF_3$, and alkoxy are preferred ones). However, in some preferred compound alkyl has no substituent.

"Cycloalkyl" means a non-aromatic monocyclic ring system comprising 3 to about 6 carbon atoms. Non-limiting examples of suitable monocyclic cycloalkyls include cyclopropyl, cyclopentyl and cyclohexyl. "Cycloalkyloxy" therefore means a cycloalkyl-O— group.

In case of cycloalkyl groups the "optionally substituted" means that the group may carry one or more substituent(s) usually applied in the organic chemistry for substitution of cycloalkyl groups. So, the substituted cycloalkyl groups carry one or more, e.g. 1 to 3, preferably 1 or 2 substituent(s), independently selected from the group of halogen, alkyl, alkoxy, hydroxyl, carboxyl, $CF_3$, nitro, sulphate, amino, monoalkylamino, dialkylamino and cyano (halogen, $CF_3$, alkyl and alkoxy are preferred ones). However, in some preferred compound cycloalkyl has no substituent.

"Heterocycloalkyl" means a non-aromatic monocyclic ring system comprising 3 to about 6 carbon atoms and 1 or 2 heteroatom(s) independently selected from the group of N, S and O. Non-limiting examples of suitable monocyclic heterocycloalkyls include piperidyl, pyrrolidinyl, piperazinyl, morpholinyl, thiomorpholinyl, thiazolidinyl, 1,3-dioxolanyl, 1,4-dioxanyl, oxazolinyl, tetrahydrofuranyl, tetrahydrothiophenyl and tetrahydrothiopyranyl. The hetereoatom is preferably 1 or 2 N atom(s). In a more preferred embodiment it contains only 1 N atom (pyrrolidinyl).

In case of heterocycloalkyl groups the "optionally substituted" means that the group may carry one or more substituent(s) usually applied in the organic chemistry for substitution of heterocycloalkyl groups. So, the substituted heterocycloalkyl groups carry one or more, e.g. 1 to 3, preferably 1 or 2 substituent(s), independently selected from the group of halogen, alkyl, alkoxy, hydroxyl, carboxyl, $CF_3$, nitro, sulphate, amino, monoalkylamino, dialkylamino and cyano (halogen, $CF_3$, alkyl and alkoxy are preferred ones). However, in some preferred compound heterocycloalkyl has no substituent.

The term "halogen" means fluorine, chlorine, bromine or iodine.

If a substituent is built up from more than one above mentioned group, then the connection to the core structure is made through the last group; e.g. in case of diphenylmetoxy group the connection to the core structure is made through the oxygen atom of the methoxy group which is substituted with two phenyl groups. The other combined groups should be interpreted in the same manner.

In a preferred embodiment HET is 5 to 6-membered heteroaromatic group comprising 3 to 5 carbon atoms and 1 to 2 heteroatom(s) independently selected from the group consisting of N, O and S. In a more preferred embodiment HET is a 5-membered ring with 1 or 2 heteroatom atom(s) independently selected from the group consisting of N, O and S (preferably from N and S). Examples of this single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl.

The preferred meanings of the symbols applied in formula (I) are given as follows:

The structure in the meaning of HET should contain a hetero atom which can coordinate the zinc atom in the MMP enzyme. In a more preferred embodiment HET is thienyl or imidazolyl. The most preferred structures are as follows:

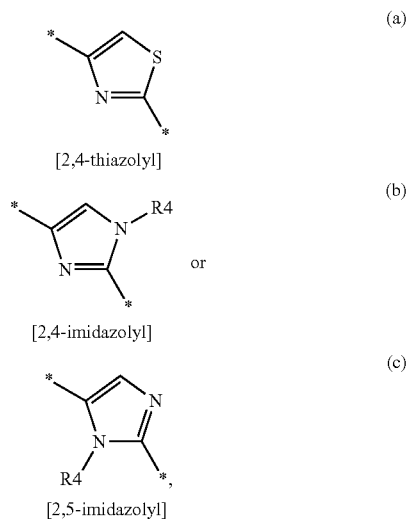

[2,4-thiazolyl] (a)

[2,4-imidazolyl] (b)

or

[2,5-imidazolyl] (c)

wherein R4 is H or $C_{1-6}$ alkyl, preferably $C_{1-3}$ alkyl, more preferably methyl.

In preferred embodiments X is $CF_3$ or COOR3, wherein R3 is H or optionally substituted $C_{1-4}$ alkyl, preferably methyl or ethyl, more preferably methyl.

The preferred embodiments of R1 are as follows:
$CH_2$-aryl, preferably benzyl,
$CH_2$-heteroaryl, preferably $CH_2$-pyridinyl,
$CH_2$-biphenyl or $CH_2$—$CH_2$-biphenyl, preferably $CH_2$-biphenyl,
diphenyl-methyl, 2,2'-diphenyl-ethyl, 3,3'-diphenyl-propyl, preferably 2,2'-diphenyl-ethyl,
C(O)—R5, where R5 is aryl or heteroaryl, preferably aryl, more preferably phenyl;
$S(O)_2$—R6, where R6 is aryl or heteroaryl, preferably aryl, more preferably phenyl, even more preferably halogen substituted phenyl, e.g. 4-F-phenyl;
where the above groups are optionally substituted with halogen, preferably with fluorine in the aromatic part (see e.g. in the meaning of $S(O)_2$—R6).

The preferred embodiments of R2 are as follows:
O—$CH_2$-aryl, preferably O-benzyl,
O—$CH_2$-heteroaryl, preferably O—$CH_2$-pyridinyl,
O—($C_{1-6}$ alkyl) which is optionally substituted with 1 or 2 aryl group(s), preferably with 2 phenyl groups, more preferably it is a diphenylmethoxy group,
where the above groups are optionally substituted with halogen, preferably with fluorine in the aromatic part.

In a preferred embodiment of the above compounds Z is N and m and n is 1, 2 or 3, more preferably 1. Typically R1 is H in these compounds.

In another preferred group of the above compounds Z is CH and n is 0 and m is 1, 2 or 3, more preferably 1. Typically R1 is H in these compounds.

In another preferred group of the above compounds the Z(R1) part stands for a covalent bond (in this case the HET ring and the benzene ring being at the other side of formula (I) are bound together directly with a covalent bond, i.e. there is no bridging atom between the rings) and n is 0 and m is 0.

It is emphasized that any above preferred (advantageous) symbol meaning can be combined with one or more another preferred (advantageous) symbol meaning(s) and such a combination results in a further advantageous embodiment (e.g. those compounds are preferred (advantageous), obviously, wherein the meanings of HET, R1 and R2 are chosen from the above list of preferred meanings).

General formula (I) embraces the following forms of the invented compounds:
salts (especially the pharmaceutically acceptable salts),
solvates (especially hydrates);
tautomeric forms;
regioisomeric forms (especially stereoisomers),
polymorphic forms,
prodrugs.

Reference to a compound of formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are known.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydro-abietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All acid and base salts are considered equivalent to the free forms of the corresponding compounds for purposes of the invention.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The tautomeric forms of compounds of formula (I) are also within the scope of this invention.

All stereoisomers (for example, geometric isomers, optical isomers and the like) of the present compounds of formula (I) (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The term "prodrug", as employed herein, denotes a compound that is a drug precursor, which upon administration to a subject, undergoes chemical conversion by metabolic or chemical processes to yield a compound of formula (I) or a salt and/or solvate thereof. A discussion of prodrugs is provided in T. Higuchi and V. Stella, Pro-drugs as Novel Delivery Systems (1987) Volume 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

The compounds of general formula (I) have been identified as new drugs for prevention and/or treatment of a variety of diseases where pathological activation of different MMP isoenzymes especially MMP2, MMP9, and MMP13 are involved including (i) cardiovascular diseases, especially acute myocardial infarction, angina pectoris, chronic myocardial infarction, dilated cardiomyopathy of various etiology including myocarditis and coronary heart disease, heart failure, atherosclerosis; (ii) tumors, especially colon, ovarian, lung, breast, cancers, melanoma, brain tumors, tumor growths and progression, tumor-induced osteolysis; (iii) brain injury and neurodegeneration; (iv) Inflammatory disorders including rheumatoid arthritis, gastritis, inflammatory hyperalgesia; (v) pathologies where ischemia and/or reperfusion injury is involved in the development of the pathology, especially myocardial infarction, stroke, kidney and liver ischemia, peripheral vessel disease, skin ischemia; (vi) eye, skin, and mucosa diseases where topical administration of MMP inhibitors is useful. The compounds of formula (I) have a cytoprotective effect which is especially useful in the prevention and/or treatment of the mentioned diseases. The found cytoprotective effect is especially useful in case of the diseases (pathologies) mentioned in above subpoint (v).

The present invention also relates to pharmaceutical compositions (for oral, intravenous, topical, subcutaneous and other known type of administration) containing at least one compound of general formula (I) as active ingredient together with one or more usual pharmaceutical auxiliary material(s). Formally another subject is the use of the compounds of general formula (I) in preparing such compositions. The applicable auxiliary materials are those which are generally applied in the preparation of pharmaceutical compositions, e.g. carriers, diluents, vehicles, coloring agents, flavoring agents, stabilizers, surfactants, carriers for the preparation of sustained release compositions etc. Further details can be found in the following book: Comprehensive Medicinal Chemistry (Corwin Hansch; Chairman of Editorial Board), Pergamon Press 1990, Volume 5., Chapter 25.2).

The invented compounds can be applied in medical methods (methods of treatment) in which a therapeutically effective amount of at least one compound of general formula (I) is administered to a patient in the need thereof for the prevention and/or treatment of an above-mentioned infection, especially mycobacterial-related disease. The "therapeutically effective amount" is meant to describe an amount of compound or a composition according to the present invention which produces the desired therapeutic effect in a suitable patient. "Patient" includes both human beings and animals. The determination of the applicable dosage is within the knowledge of a skilled medical practician.

EXAMPLES

Example 1

2-({[(4-Fluorophenyl)methyl]({[4-(pyridin-3-yl-methoxy)phenyl]methyl})amino}methyl)-1,3-thiazole-4-carboxylic acid (Compound 1)

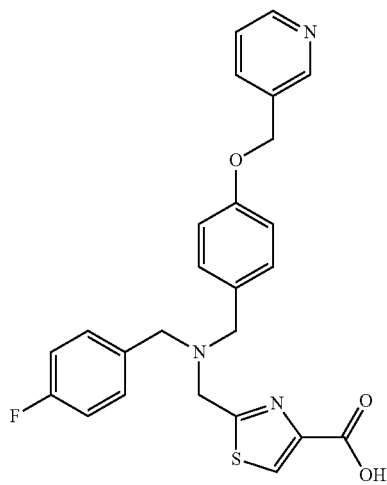 [SMILES: O=C(O)c1csc(CN(Cc2ccc(F)cc2)Cc2ccc(OCc3cccnc3)cc2)n1]

A solution of 0.12 g (0.24 mmol) ethyl 2-({[(4-fluorophenyl)methyl]({[4-(pyridin-3-ylmethoxy)phenyl]methyl})amino}methyl)-1,3-thiazole-4-carboxylate (see Compound 2), 1 ml of methanol and 1 ml of 20% aqueous sodium hydroxide was stirred for 1.5 hours at 60-65° C. After cooling the obtained mixture to ambient temperature 2 ml of water is added, followed by the evaporation of methanol in vacuum. The solution is than acidified with 10% aqueous hydrochloric acid to pH 7.5 and extracted with chloroform several times. The collected organic layers were combined and dried on sodium sulfate and evaporated to dryness.

Yield: 0.104 g (0.22 mmol, 92%)

MS (M+1): 464

NMR (DMSO-d6): 8.65 (1H, m), 7.88 (1H, d), 7.0-7.5 (11H, m), 5.08 (2H, s), 4.11 (2H, s), 3.62 (2H, s), 3.47 (2H, s).

Example 2

Ethyl 2-({[(4-fluorophenyl)methyl]({[4-(pyridin-3-ylmethoxy)phenyl]methyl})amino}methyl)-1,3-thiazole-4-carboxylate (Compound 2)

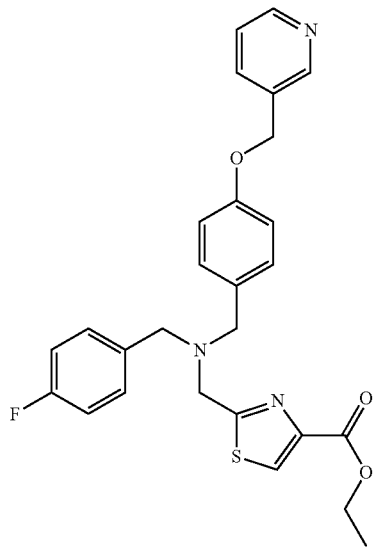 [SMILES: CCOC(=O)c1csc(CN(Cc2ccc(F)cc2)Cc2ccc(OCc3cccnc3)cc2)n1]

In 15 ml of freshly distillated acetonitrile 0.97 g (3 mmol) [(4-fluorophenyl)methyl]({[4-(pyridin-3-ylmethoxy)phenyl]methyl})amine (see Compound 3) is dissolved. To this solution 0.62 g (3 mmol) ethyl 2-(chloromethyl)-1,3-thiazole-5-carboxylate (available: Albany Molecular Res. ALB H02106432) and 1.24 g (9 mmol) potassium carbonate is added followed by addition of 0.5 g (3 mmol) powdered potassium iodide and the resulted mixture is refluxed for one hour. The obtained solution is cooled and the precipitated inorganics are removed by filtration. The filtrate is evaporated in vacuum and the residue is dissolved in chloroform and washed with 3 portions of water. The organic layer is dried over sodium sulfate and evaporated. The crude product (1.77 g) is purified by silica gel column chromatography using of chloroform:methanol=50:1 as eluent.

Yield: 0.94 g (1.9 mmol, 64%)

MS (M+1): 492

Example 3

[(4-Fluorophenyl)methyl]({[4-(pyridin-3-ylmethoxy)phenyl]methyl})amine (Compound 3)

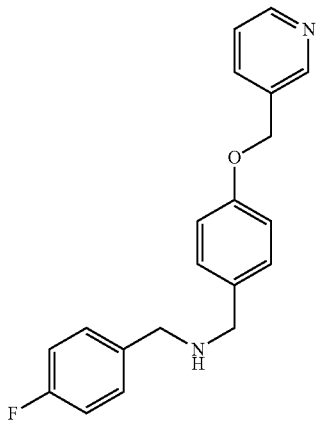 [SMILES: Fc1ccc(CNCc2ccc(OCc3cccnc3)cc2)cc1]

A mixture of 1.8 g of 4-(pyiridin-3-ylmethoxy)benzaldehyde (8.5 mmol, see Compound 4), 1.06 g of 4-fluorobenzylamine (0.97 ml, 8.5 mmol) and 40 ml of absolute ethanol is stirred at 80° C. for 16 hours. The mixture is cooled to room temperature and 0.38 g of sodium borohydride is added (10 mmol) portion wise in appr. 10 minutes, leaving the mixture to warm up to 35-40° C., then 30 minutes further stirred without cooling. To the mixture 1 ml of water is added and stirred for further 10 minutes. After addition of 100 ml of chloroform and 100 ml of water it is diligently shaked in a separation funnel. The organic layer was than washed twice with 100 ml of water, dried over sodium sulfate and evaporated in vacuum.

Yield: 2.0 g (6.2 mmol, 73%)

MS (M+1): 323

Example 4

4-(Pyiridin-3-ylmethoxy)benzaldehyde (Compound 4)

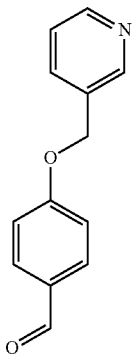 [SMILES: O=Cc1ccc(OCc2cccnc2)cc1]

To a mixture of 1.22 g (10 mmol) 4-hidroxybenzaldehyde, 1.64 g (10 mmol) 3-chloromethylpyridine hydrochloride and 20 ml of N,N-dimethyl-formamide 4.2 g (30 mmol) of anhydrous sodium carbonate is added and the reaction mixture is stirred for 2 hours at 70° C. After cooling the mixture the precipitated inorganics are removed by filtration and the solvent is evaporated in vacuum. Water added to the residue and the resulted solution is extracted by chloroform. The organic layers are collected and combined and extracted with water, dried over sodium sulfate and evaporated. The residue is crystallized using diethyl ether.

Yield: 1.54 g (7.2 mmol, 72%).

MS (M+1): 214

Example 5

2-[({[4-(Benzyloxy)phenyl]methyl}[(3-fluorophenyl)methyl]amino)methyl]-1,3-thiazole-4-carboxylic acid (Compound 5)

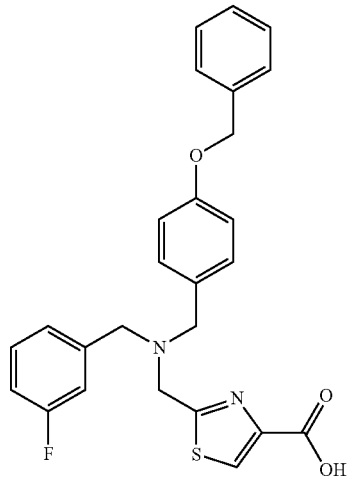 [SMILES: O=C(O)c1csc(CN(Cc2ccc(OCc3ccccc3)cc2)Cc2cccc(F)c2)n1]

The compound was prepared analogously to the process described by the reaction sequence of Examples 4, 3, 2 and 1, using benzyl-bromide instead of 3-chloromethylpyridine hydrochloride in Example 4 and 3-fluorobenzylamine instead of 4-fluorobenzylamine in Example 3.

MS (M+1): 463

Example 6

2-[({[4-(Benzyloxy)phenyl]methyl}(2,2-diphenylethyl)amino)methyl]-1,3-thiazole-4-carboxylic acid (Compound 6)

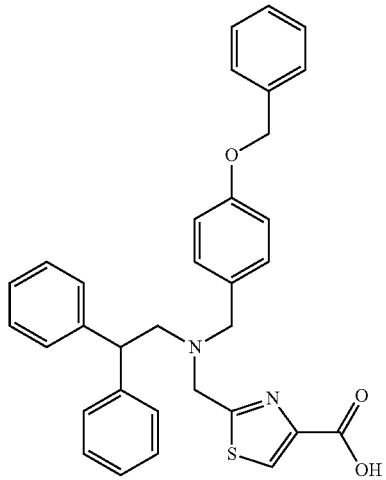 [SMILES: O=C(O)c1csc(CN(Cc2ccc(OCc3ccccc3)cc2)CC(c2ccccc2)c2ccccc2)n1]

The compound was prepared analogously to the process described by the reaction sequence of Examples 4, 3, 2 and 1, using benzyl-bromide instead of 3-chloromethylpyridine hydrochloride in example 4 and 1-amino-2,2-diphenyl ethane instead of 4-fluorobenzylamine in Example 3.

MS (M+1): 534

Example 7

2-[(Dibenzylamino)methyl]-1,3-thiazole-4-carboxylic acid (Compound 7)

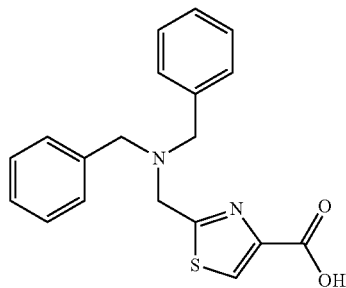 [SMILES: O=C(O)c1csc(CN(Cc2ccccc2)Cc2ccccc2)n1]

The compound was prepared analogously to the process described by the reaction sequence of Examples 4, 3, 2 and 1, using benzyl-bromide instead of 3-chloromethylpyridine hydrochloride in Example 4 and benzylamine instead of 4-fluorobenzylamine in Example 3.

MS (M+1): 339

Example 8

2-[({[4-(Pyridin-3-ylmethoxy)phenyl]methyl}[(3-fluorophenyl)methyl]amino)methyl]-1,3-thiazole-4-carboxylic acid (Compound 8)

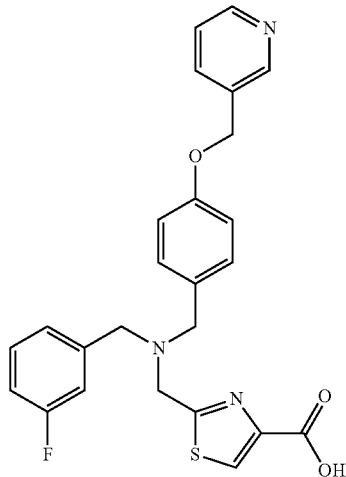 [SMILES: O=C(O)c1csc(CN(Cc2ccc(OCc3cccnc3)cc2)Cc2cccc(F)c2)n1]

The compound was prepared analogously to the process described by the reaction sequence of Examples 4, 3, 2 and 1, using 3-fluorobenzylamine instead of 4-fluorobenzylamine in Example 3.

MS (M+1): 464

Example 9

2-({[(4-Fluorophenyl)methyl]({[4-(pyridin-4-yl-methoxy)phenyl]methyl})amino}methyl)-1,3-thiazole-4-carboxylic acid (Compound 9)

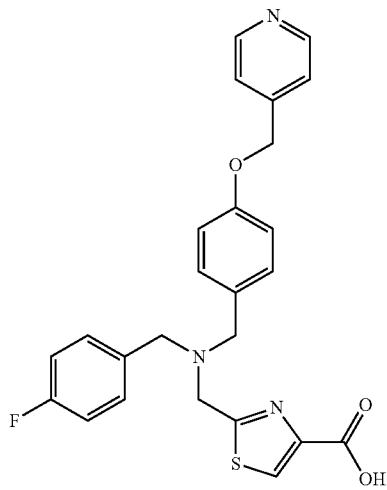 [SMILES: O=C(O)c1csc(CN(Cc2ccc(F)cc2)Cc2ccc(OCc3ccncc3)cc2)n1]

The compound was prepared analogously to the process described by the reaction sequence of Examples 4, 3, 2 and 1, using 4-chloromethylpyridine hydrochloride instead of 3-chloromethylpyridine hydrochloride in Example 4.

MS (M+1): 464

Example 10

2-[({[4-(Pyridin-3-ylmethoxy)phenyl]methyl}(pyridin-3-ylmethyl)amino)methyl]-1,3-thiazole-4-carboxylic acid (Compound 10)

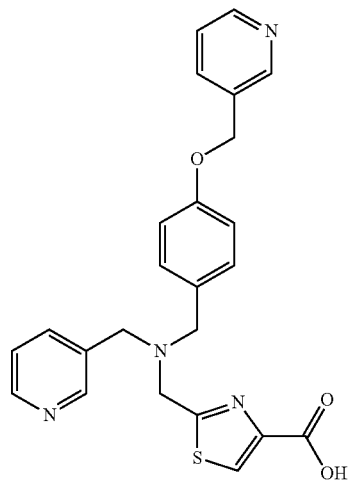 [SMILES: O=C(O)c1csc(CN(Cc2ccc(OCc3cccnc3)cc2)Cc2cccnc2)n1]

The compound was prepared analogously to the process described by the reaction sequence of Examples 4, 3, 2 and 1, using 3-chloromethylpyridine hydrochloride instead of 4-fluorobenzylamine in Example 3.

MS (M+1): 447

Example 11

Ethyl 2-[({[4-(benzyloxy)phenyl]methyl}[(4-fluorophenyl)methyl]amino)methyl]-1,3-thiazole-4-carboxylate (Compound 11)

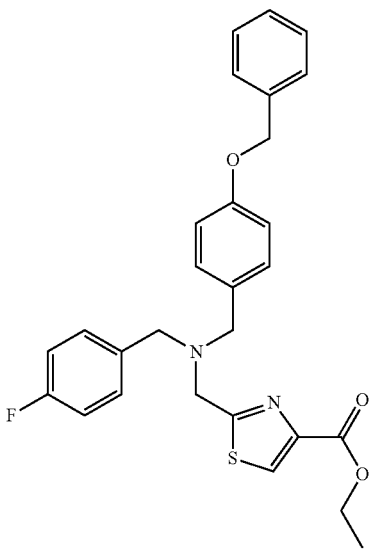

The compound was prepared analogously to the process described by the reaction sequence of Examples 4, 3, and 2, using benzyl-bromide instead of 3-chloromethylpyridine hydrochloride in Example 4.

MS (M+1): 499

Example 12

2-{[(Pyridin-3-ylmethyl)({[4-(pyridin-4-ylmethoxy)phenyl]methyl})amino]methyl}-1,3-thiazole-4-carboxylic acid (Compound 12)

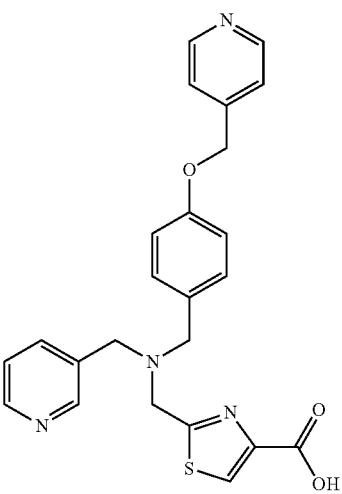 [SMILES: O=C(O)c1csc(CN(Cc2ccc(OCc3ccncc3)cc2)Cc2cccnc2)n1]

The compound was prepared analogously to the process described by the reaction sequence of Examples 4, 3, 2 and 1, using 4-chloromethylpyridine hydrochloride instead of 3-chloromethylpyridine hydrochloride. In Example 4 and 3-chloromethylpyridine hydrochloride instead of 4-fluorobenzylamine in Example 3.

MS (M+1): 447

Example 13

2[({[4-(Benzyloxy)phenyl]methyl}(pyridin-4-ylmethyl)amino)methyl]-1,3-thiazole-4-carboxylic acid
(Compound 13)

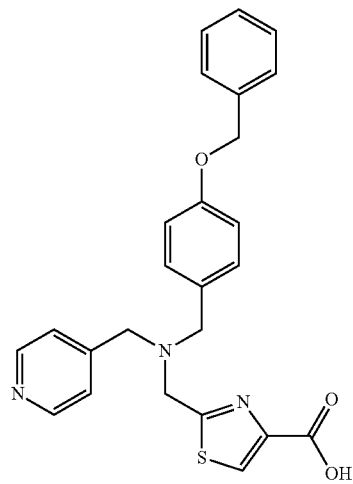 [SMILES: O=C(O)c1csc(CN(Cc2ccncc2)Cc2ccc(OCc3ccccc3)cc2)n1]

The compound was prepared analogously to the process described by the reaction sequence of Examples 4, 3, 2 and 1, using benzyl-bromide instead of 3-chloromethylpyridine hydrochloride in Example 4 and 4-chloromethylpyridine hydrochloride instead of 4-fluorobenzylamine in Example 3.

MS (M+1): 446

Example 14

2-[({[4-(Benzyloxy)phenyl]methyl}(pyridin-3-ylmethyl)amino)methyl]-1,3-thiazole-4-carboxylic acid
(Compound 14)

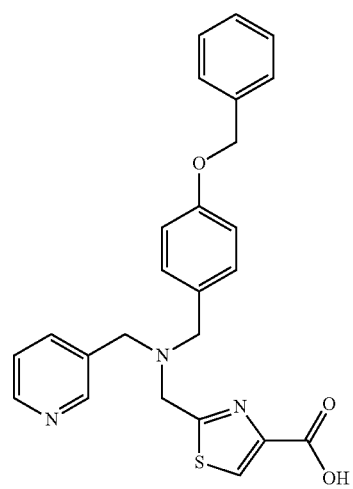 [SMILES: O=C(O)c1csc(CN(Cc2ccc(OCc3ccccc3)cc2)Cc2cccnc2)n1]

The compound was prepared analogously to the process described by the reaction sequence of Examples 4, 3, 2 and 1, using benzyl-bromide instead of 3-chloromethylpyridine hydrochloride in Example 4 and 3-chloromethylpyridine hydrochloride instead of 4-fluorobenzylamine in Example 3.

MS (M+1): 446

Example 15

2-({[(4-Fluorophenyl)methyl][(4-biphenyl)methyl]amino}methyl)-1,3-thiazole-4-carboxylic acid
(Compound 15)

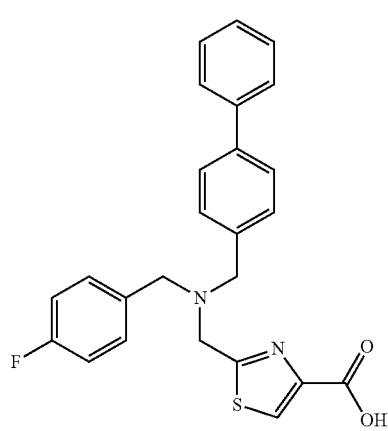 [SMILES: O=C(O)c1csc(CN(Cc2ccc(F)cc2)Cc2ccc(-c3ccccc3)cc2)n1]

The compound was prepared analogously to the process described in Example 1, using compound 32 as starting material.

MS (M+1): 433

Example 16

Ethyl 2-[({[4-(benzyloxy)phenyl]methyl}(pyridin-3-ylmethyl)amino)methyl]-1,3-thiazole-4-carboxylate
(Compound 16)

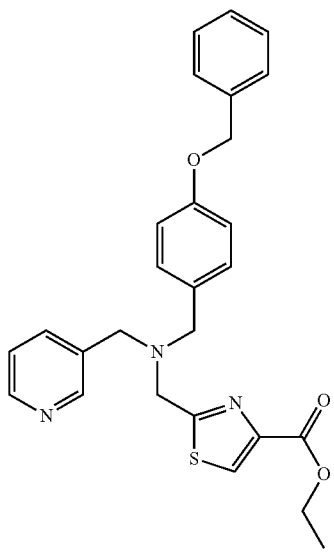 [SMILES: CCOC(=O)c1csc(CN(Cc2ccc(OCc3ccccc3)cc2)Cc2cccnc2)n1]

The compound was prepared analogously to the process described by the reaction sequence of Examples 4, 3 and 2, using benzyl-bromide instead of 3-chloromethylpyridine hydrochloride in Example 4 and 3-chloromethylpyridine hydrochloride instead of 4-fluorobenzylamine in Example 3.

MS (M+1): 474

Example 17

Ethyl 2-[({[4-(pyridin-3-ylmethoxy)phenyl]methyl}(pyridin-3-ylmethyl)amino)methyl]-1,3-thiazole-4-carboxylate (Compound 17)

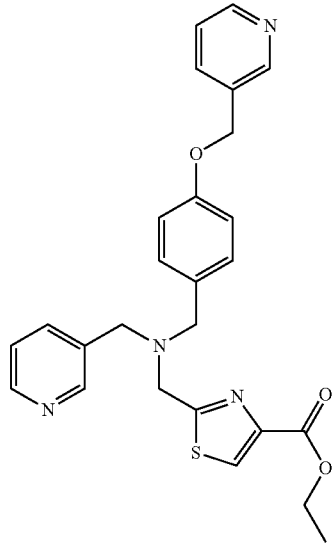 [SMILES: CCOC(=O)c1csc(CN(Cc2ccc(OCc3cccnc3)cc2)Cc2cccnc2)n1]

The compound was prepared analogously to the process described by the reaction sequence of Examples 4, 3 and 2, using 3-chloromethylpyridine hydrochloride instead of 4-fluorobenzylamine in Example 3.

MS (M+1): 475

Example 18

Ethyl 2-({[(4-fluorophenyl)methyl]({[4-(pyridin-4-ylmethoxy)phenyl]methyl})amino}methyl)-1,3-thiazole-4-carboxylate (Compound 18)

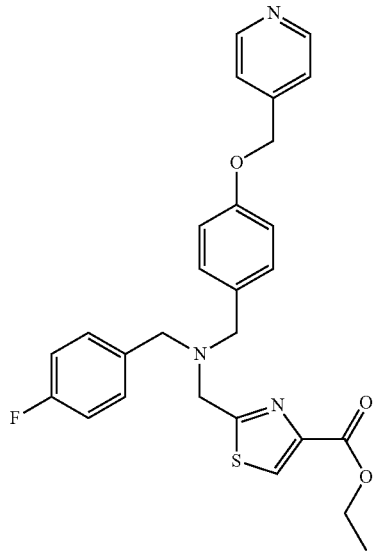 [SMILES: CCOC(=O)c1csc(CN(Cc2ccc(F)cc2)Cc2ccc(OCc3ccncc3)cc2)n1]

The compound was prepared analogously to the process described by the reaction sequence of Examples 4, 3 and 2, using 4-chloromethylpyridine hydrochloride instead of 3-chloromethylpyridine hydrochloride in Example 4.

MS (M+1): 492

Example 19

Ethyl 2-{[(pyridin-3-ylmethyl)({[4-(pyridin-4-ylmethoxy)phenyl]methyl})amino]methyl}-1,3-thiazole-4-carboxylate (Compound 19)

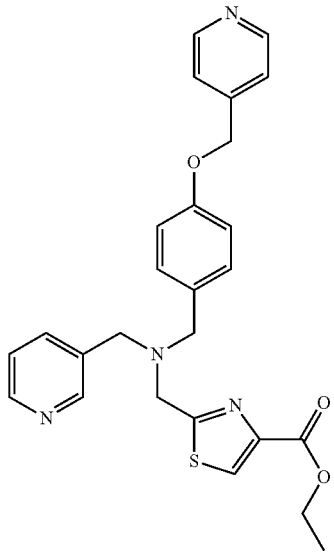 [SMILES: CCOC(=O)c1csc(CN(Cc2ccc(OCc3ccncc3)cc2)Cc2cccnc2)n1]

The compound was prepared analogously to the process described by the reaction sequence of Examples 4, 3 and 2, using 4-chloromethylpyridine hydrochloride instead of 3-chloromethylpyridine hydrochloride in Example 4 and 3-chloromethylpyridine hydrochloride instead of 4-fluorobenzylamine in Example 3.

MS (M+1): 475

Example 20

Ethyl 2-[({[4-(benzyloxy)phenyl]methyl}(pyridin-4-ylmethyl)amino)methyl]-1,3-thiazole-4-carboxylate (Compound 20)

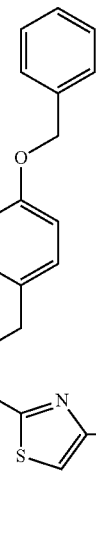

The compound was prepared analogously to the process described by the reaction sequence of Examples 4, 3 and 2, using benzyl-bromide instead of 3-chloromethylpyridine hydrochloride in Example 4 and 4-chloromethylpyridine hydrochloride instead of 4-fluorobenzylamine in Example 3.

MS (M+1): 474

Example 21

2-{[(4-Benzyloxy-benzyl)-(4-fluoro-benzyl)-amino]-methyl}-thiazole-4-carboxylic acid ethylamide (Compound 21)

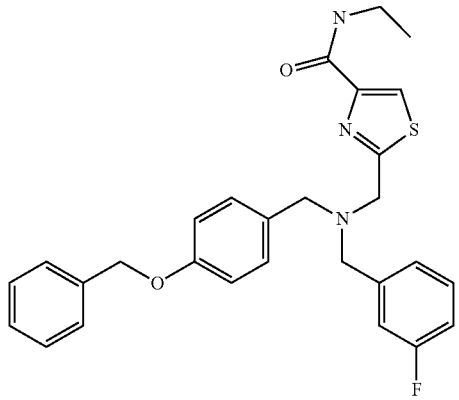 [SMILES: CCNC(=O)c1csc(CN(Cc2ccc(OCc3ccccc3)cc2)Cc2cccc(F)c2)n1]

463 mg (1 mmol) 2-[({[4-(benzyloxy)phenyl]methyl}[(3-fluorophenyl)methyl]amino)methyl]-1,3-thiazole-4-carboxylic acid (Compound 5) was dissolved in 2 ml dimethyl formamide (DMF). To this solution 418 mg (1.1 mmol) O-(7-azabenzotriazol-1-yl)-N,N,N',N'-tetramethyluronium hexafluorophosphate (HATU) was added. The solution was stirred for 1 hour. Then 0.5 ml ethylamine was added (in excess) and the reaction was stirred at 60° C. for overnight. The solvent was removed with several washing and digeration with water/hot water and the product was chromatographed on silica gel using chloroform/methanol 8/1 as eluent. Yield: 235 mg (46%).

MS (M+1): 489+1

Example 22

2-[({[4-(Diphenylmethoxy)phenyl]methyl}[(4-fluorophenyl)methyl]amino)methyl]-1H-imidazole-4-carboxylic acid (Compound 22)

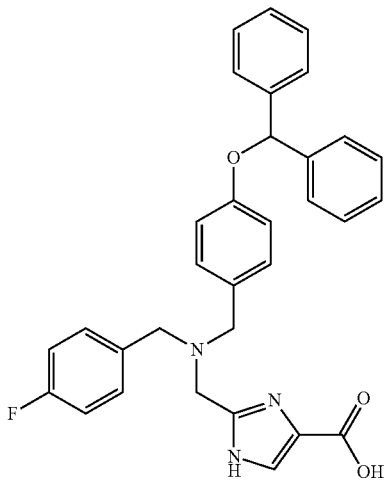 [SMILES: O=C(O)c1c[nH]c(CN(Cc2ccc(F)cc2)Cc2ccc(OC(c3ccccc3)c3ccccc3)cc2)n1]

A mixture of 0.6 g (1 mmol) of {[4-(diphenylmethoxy)phenyl]methyl}[(4-fluorophenyl)me-thyl]{[4-(trifluoromethyl)-1H-imidazol-2-yl]methyl}amine (Compound 23), 15 ml of methanol and 9 ml of sodium methoxide (as 2N methanolic solution) is heated for 35 minutes at 100° C. in a sealed pressure tube. Upon cooling 100 ml of 0.1N hydrochloric is added, and the product is extracted using 90 ml of chloroform. The organic layer is washed twice with water, dried on sodium sulfate and evaporated. The crude product (0.6 g) containing the mixture of corresponding ester and orthoester is stirred in mixture of 3.5 ml 40% aqueous sodium hydroxide, 10 ml of methanol and 6 ml of N,N-dimethyl-formamide at 70° C. for 2 days. Upon cooling the pH of the mixture is adjusted to 4.5 using hydrochloric acid and extracted with ethyl acetate. The collected organic layers are combined and dried on sodium sulfate and evaporated. The crude product is purified using column chromatography on using chloroform:methanol=8:1 as eluent. Yield: 0.12 g (0.23 mmol, 23%).

MS (M+1): 522

NMR: (MG-261) DMSO (d6): 7.10-7.35 (11H, m), 7.02-7.06 (1H, m), 6.9 (2H, dd), 7.35 (1H, s), 5.11 (2H, s), 4.1 (2H, s), 3.52 (2H, s), 3.47 (2H, s).

Example 23

{[4-(Diphenylmethoxy)phenyl]methyl}[(4-fluorophenyl)methyl]{[4-(trifluoromethyl)-1H-imidazol-2-yl]methyl}amine (Compound 23)

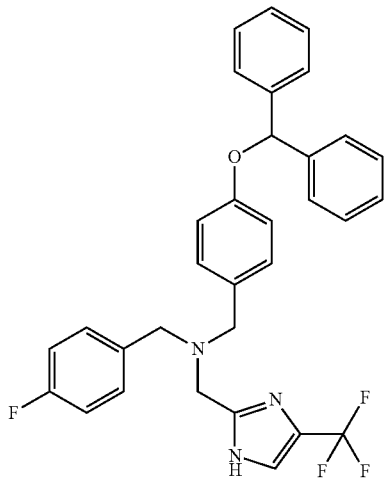 [SMILES: Fc1ccc(CN(Cc2ccc(OC(c3ccccc3)c3ccccc3)cc2)Cc2nc(C(F)(F)F)c[nH]2)cc1]

4-Fluoro-benzylchloride (0.24 ml) is added to a solution of 0.88 g (2 mmol) {[4-(diphenylmethoxy)phenyl]methyl} ({[4-(trifluoromethyl)-1H-imidazol-2-yl]methyl})amine (Compound 24), 20 ml of chloroform and 0.56 g of potassium carbonate and the mixture is stirred at 65° C. for 6 days. The mixture is diluted with chloroform, washed with water three times and dried over sodium sulfate. The solvent is removed in vacuum and the crude product is purified by column chromatography on silica gel using chloroform as eluent.

Yield: 0.3 g (0.55 mmol, 28%)

MS (M+1): 546

Example 24

{[4-(Diphenylmethoxy)phenyl]methyl}({[4-(trifluoromethyl)-1H-imidazol-2-yl]methyl})amine (Compound 24)

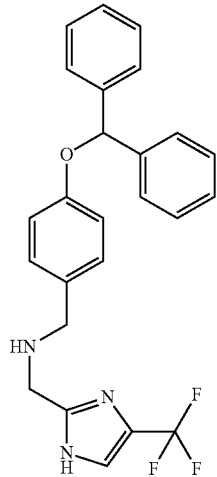 [SMILES: FC(F)(F)c1c[nH]c(CNCc2ccc(OC(c3ccccc3)c3ccccc3)cc2)n1]

To a solution of 3.98 g (15 mmol) of terc-butil-N-{[4-(trifluorometil)-1H-imidazol-2-yl]mehyl}carbamate in 30 ml of dichloromethane at 0° C. 21 ml of 16% hydrochloride acid/ethylacetate solution is added and the reaction mixture is stirred at room temperature for half an hour. Then the solution is evaporated half to its original volume in vacuum and 60 ml of diethyl ether is added. The precipitated crystals are filtered off and dried in vacuum desiccator over sodium hydroxide.

The dried amino imidazole product is dissolved in 60 ml of ethanol the pH is adjusted to 6-6.5 using 2N sodium methoxide in methanolic solution and 4.32 g (15 mmol) of 4-(diphenylmetoxi)benzaldehyde (Compound 25) is added and the mixture is stirred at 80° C. for 2 hours. Upon cooling 0.66 g (17.8 mmol) of sodium borohydride is added. The mixture is subsequently stirred for 30 minutes at room temperature and 3 ml of water is added to eliminate the remaining borohydride and stirred 10 minutes while completing the reaction. Upon addition of 180 ml chloroform the mixture is extracted three times with 180 ml of water and dried over sodium sulfate and the solvent is removed in vacuum. The crude product is purified by column chromatography using silica gel and chloroform:methanol=20:1 mixture as eluent. Yield: 4.1 g (9.4 mmol, 63%)

MS (M+1): 438

Example 25

4-(Diphenylmethoxy)benzaldehyde (Compound 25)

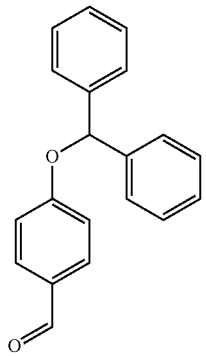 [SMILES: O=Cc1ccc(OC(c2ccccc2)c2ccccc2)cc1]

A mixture of 9.88 g (40 mmol) of bromo-diphenylmethane, 100 ml of N,N-dimethyl formamide, 16.8 g powdered potassium carbonate and 5.36 g (44 mmol) of 4-hydroxibenzaldehyde is stirred at 90° C. for 16 hours. Upon cooling the precipitated inorganic salts are removed by filtration and the obtained solution is evaporated to dryness. The residue is dissolved in 150 ml ethyl acetate, washed sequentially consecutively with water and 5% aqueous sodium hydroxide solution and twice with water. The solution is dried over sodium sulfate, evaporated in vacuum; the residue is dissolved in small amount of ethyl acetate. The product crystallized upon addition of small amount of hexane.

Yield: 7.0 g (24 mmol, 61%).

Example 26

{[4-(Benzyloxy)phenyl]methyl}[(4-fluorophenyl)methyl]{[1-methyl-4-(trifluoromethyl)-1H-imidazol-2-yl]methyl}amine (Compound 26)

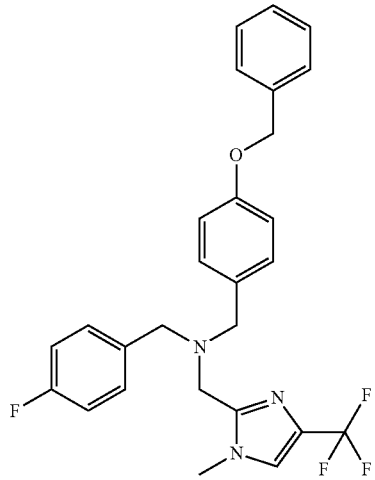 [SMILES: Cn1cc(C(F)(F)F)nc1CN(Cc1ccc(F)cc1)Cc1ccc(OCc2ccccc2)cc1]

{[4-(Benzyloxy)phenyl]methyl}[(4-fluorophenyl)methyl]{[4-(trifluoromethyl)-1H-imidazol-2-yl]methyl}amine (Compound 27, 240 mg) was dissolved in 5 ml dry methanol. To the solution 1 ml 2N NaOMe in MeOH was added followed by the addition of 0.5 ml MeI. The solution was stirred at room temperature overnight. After evaporation of the residue the product was washed with diethyl ether to give the title compound as white crystals.

Yield: 185 mg (83%).

MS (M+1): 484

Example 27

{[4-(Benzyloxy)phenyl]methyl}[(4-fluorophenyl)methyl]{[4-(trifluoromethyl)-1H-imidazol-2-yl]methyl}amine (Compound 27)

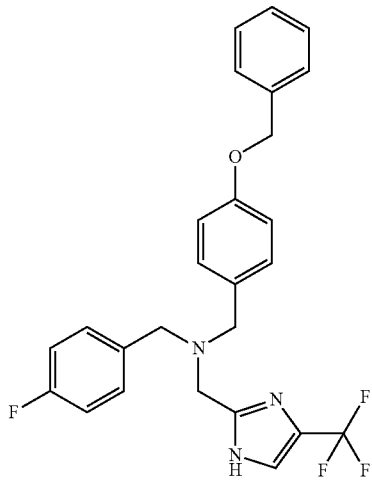 [SMILES: Fc1ccc(CN(Cc2ccc(OCc3ccccc3)cc2)Cc2nc(C(F)(F)F)c[nH]2)cc1]

The compound was prepared analogously to the process described by the reaction sequence of Examples 25, 24 and 23, using benzyl-bromide instead of bromo-diphenylmethane in Example 25.

MS (M+1): 470

Example 28

2-[(4-Benzyloxy-benzylamino)-methyl]-thiazole-4-carboxylic acid methyl ester (Compound 28)

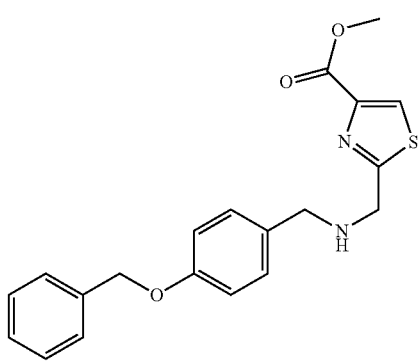 [SMILES: COC(=O)c1csc(CNCc2ccc(OCc3ccccc3)cc2)n1]

The compound was prepared analogously to the process described by the reaction sequence of Examples 4 and 3 using benzyl-bromide instead of 3-chloromethylpyridine hydrochloride in Example 4 and 2-aminomethyl-thiazole-4-carboxylic acid methyl ester hydrochloride (commercially available at Otava chemicals) instead of 4-fluorobenzylamine in Example 3.

MS (M+1): 382+1

Example 29

{[4-(Benzyloxy)phenyl]methyl}([{4-(trifluoromethyl)-1H-imidazol-2-yl]methyl})amine (Compound 29)

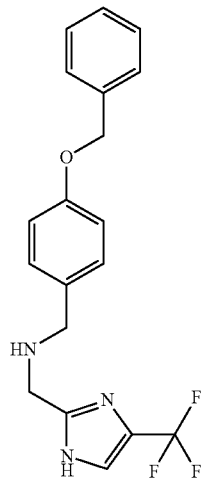

The compound was prepared analogously to the process described by the reaction sequence of Examples 25 and 24 using benzyl-bromide instead of bromo-diphenylmethane in Example 25.

MS (M+1): 362

Example 30

2-[({[4-(Benzyloxy)phenyl]methyl}[(4-fluorophenyl)methyl]amino)methyl]-1H-imidazole-4-carboxylic acid (Compound 30)

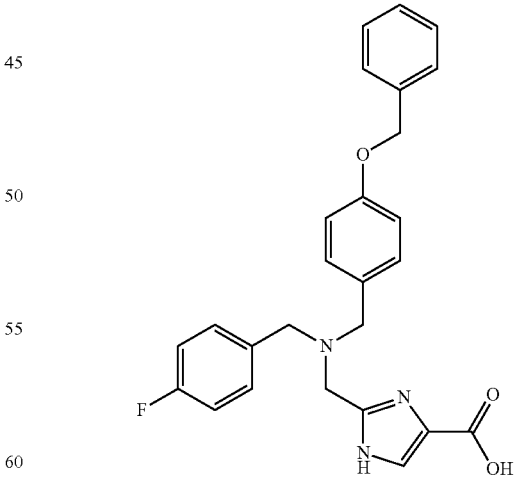

The compound was prepared analogously to the process described by the reaction sequence of Examples 25, 24, 23 and 22, using benzyl-bromide instead of bromo-diphenylmethane in Example 25.

MS (M+1): 446

Example 31

2-[({[4-(Pyridin-3-ylmethoxy)phenyl]methyl}amino)methyl]-1H-imidazole-4-carboxylic acid (Compound 31)

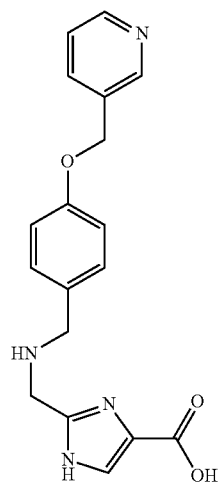 [SMILES: O=C(O)c1c[nH]c(CNCc2ccc(OCc3cccnc3)cc2)n1]

The compound was prepared analogously to the process described by the reaction sequence of Examples 25, 24 and 22, using 3-chloromethyl pyridine hydrochloride instead of bromo-diphenylmethane in Example 25.

MS (M+1): 339

Example 32

2-{[Biphenyl-4-ylmethyl-(4-fluoro-benzyl)-amino]-methyl}-thiazole-4-carboxylic acid ethylester (Compound 32)

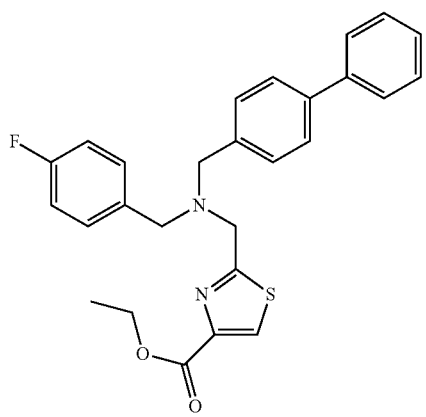 [SMILES: CCOC(=O)c1csc(CN(Cc2ccc(F)cc2)Cc2ccc(-c3ccccc3)cc2)n1]

The compound was prepared analogously to the process described in the reaction sequence: Compounds 4, 3, 2. Using Biphenyl-4-carbaldehyde instead of 4-(Pyiridin-3-ylmethoxy)benzaldehyde (Compound 3).

MS: (M+1): 461

Example 33

2-{[(4-benzyloxy-benzyl)-benzenesulfonyl-amino]-methyl}thiazole-4-carboxylic acid ethyl ester (Compound 33)

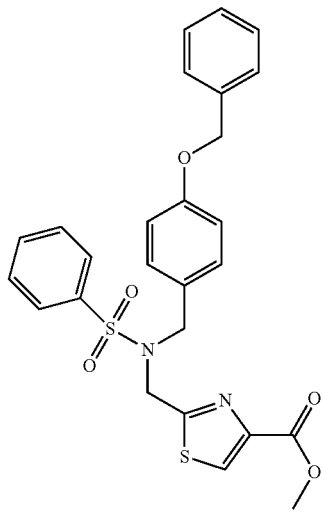 [SMILES: COC(=O)c1csc(CN(Cc2ccc(OCc3ccccc3)cc2)S(=O)(=O)c2ccccc2)n1]

2-[(4-Benzyloxy-benzylamino)-methyl]-thiazole-4-carboxylic acid methyl ester (Compound 28, 382 mg, 1 mmol) was dissolved in 5 ml of dichloromethane, 276 mg (2 mmol) potassium carbonate powder was added, and to the obtained suspension solution of 176 mg (1 mmol) benzenesulfonyl-chloride in 2 ml DCM was added dropwise at room temperature. The solution was stirred for 2 hours. The solids were filtered off, the solid residue was washed with DCM and the combined organic phase was further washed with water. The organic phase was dried, evaporated to dryness and purified by column chromatography (EtOAc:Hexane=1:4). Yield: 280 mg (60%).

MS (M+1): 508+1

Example 34

2-{[(4-Benzyloxy-benzyl)-(4-fluorobenzoyl)-amino]-methyl}-thiazole-4-carboxylic acid ethyl ester (Compound 34)

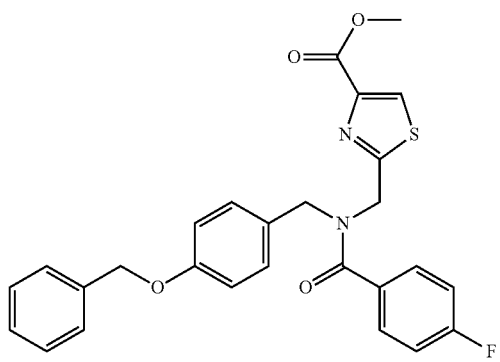 [SMILES: COC(=O)c1csc(CN(Cc2ccc(OCc3ccccc3)cc2)C(=O)c2ccc(F)cc2)n1]

2-[(4-Benzyloxy-benzylamino)-methyl]-thiazole-4-carboxylic acid methyl ester (Compound 28, 382 mg, 1 mmol) was dissolved in 5 ml of dichloromethane, 276 mg (2 mmol) potassium carbonate powder was added, and to the obtained suspension solution of 158 mg (1 mmol) 4-fluoro benzoyl-chloride in 2 ml DCM was added dropwise at room temperature. The solution was stirred for 2 hours. The solids were filtered off, the solid residue was washed with DCM and the combined organic phase was further washed with water. The organic phase was dried, evaporated to dryness and purified by column chromatography (EtOAc:Hexane=1:4). Yield: 280 mg (52%).

MS (M+1): 490+1

Example 35

2-Phenethyl-5-trifluoromethyl-1H-imidazole (Compound 35)

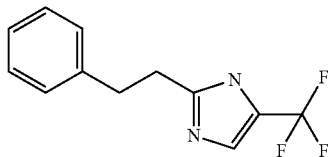 [SMILES: FC(F)(F)c1cnc(CCc2ccccc2)[nH]1]

13.4 g (50 mmol) of 1,1-dibromo-3,3,3-trifluoro acetone was dissolved in 45 ml of 15% by weight aqueous sodium acetate solution. It was stirred at 90° C. for 30 minutes, and then cooled to ambient temperature and 5.85 g (45 mmol) of 3-phenyl propanal was added, dissolved previously in the mixture of 227 ml methanol and 60 ml cc. aqueous ammonia. The reaction mixture was stirred overnight. Then the methanol was evaporated. The remaining aqueous phase was extracted with ethylacetate and the organic phase was further washed with water. The organic phase was dried, evaporated to about 10% of the original volume. The precipitated product was filtered, washed with water and hexane. Yield: 9.3 g (86%).

MS: (M+1): 241.

Example 36

2-Phenethyl-3H-imidazole-4-carboxylic acid (Compound 36)

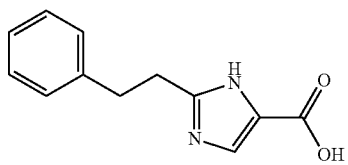 [SMILES: O=C(O)c1cnc(CCc2ccccc2)[nH]1]

11.7 g (0.5 mol) of sodium was dissolved in 400 ml of methanol. To this solution 6 g (28 mmol) of 2-phenyl-5-trifluoromethyl-1H-imidazole (Example 35) was added. The solution was placed in a stainless steel autoclave and was heated to 150° C. overnight. After the reaction mixture cooled back to ambient temperature it was neutralized with 10% aqueous HCl and its pH was set to 6. The solution is evaporated to dryness. The residue was extracted with chloroform and washed with water. The product was found in the aqueous phase after extraction, so the aqueous phase was evaporated to dryness and the residue was washed with THF. After evaporating the THF the product was obtained in 845 mg (yield: 14%).

MS: (M+1): 217.

Example 37

2-Phenethyl-3H-imidazole-4-carboxylic acid methyl ester (Compound 37)

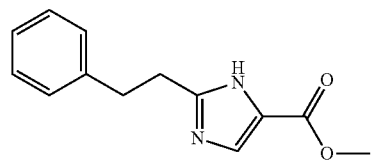 [SMILES: COC(=O)c1cnc(CCc2ccccc2)[nH]1]

11.7 g (0.5 mol) of sodium was dissolved in 400 ml of methanol. To this solution 6 g (28 mmol) of 2-phenyl-5-trifluoromethyl-1H-imidazole (Example 35) was added. The solution was placed in a stainless steel autoclave and was heated to 100° C. overnight. After the reaction mixture cooled back to ambient temperature it was neutralized with 10% aqueous HCl and its pH was set to 6. The product precipitated upon adding water, then filtered, further washed with water and dried to give 2.41 g of the targeted product (Yield: 37%).

MS: (M+1): 231.

Example 38

(2-Phenethyl-3H-imidazol-4-yl)-pyrrolidin-1-yl-methanone (Compound 38)

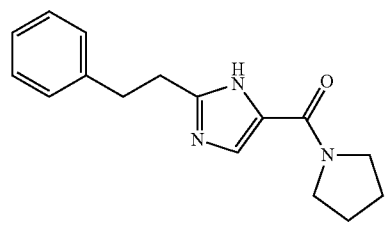 [SMILES: O=C(c1cnc(CCc2ccccc2)[nH]1)N1CCCC1]

230 mg (1 mmol) of 2-Phenethyl-3H-imidazole-4-carboxylic acid methyl ester was dissolved in 5 ml pyrrolidine. The solution was refluxed overnight. Then the product precipitated upon adding water, then filtered, further washed with water and dried to give 195 mg of the targeted product (Yield: 71%).

MS: (M+1): 270
MS: (M+1): 270

Example 39

2-Phenyl-5-trifluoromethyl-1H-imidazole (Compound 39)

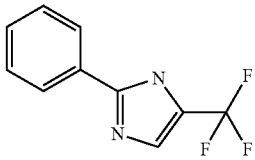 [SMILES: FC(F)(F)c1cnc(-c2ccccc2)[nH]1]

13.4 g (50 mmol) of 1,1-dibromo-3,3,3-trifluoro acetone was dissolved in 8.18 g of 15 w % (% by weight) aqueous sodium acetate solution). It was stirred at 90° C. for 30 minutes, then cooled to ambient temperature, and 4.77 g (45 mmol) of benzaldehyde was added previously dissolved in the mixture of 227 ml methanol and 60 ml cc. aqueous ammonia. The reaction mixture was stirred overnight. Then the methanol was evaporated. The remaining aqueous phase was extracted with ethylacetate and the organic phase was further washed with water. The organic phase was dried, evaporated to about 10% of the original volume. The precipitated product was filtered, washed with water and hexane. Yield: 10.7 g (99%).

MS (M+1): 213

Example 40

2-Phenyl-3H-imidazole-4-carboxylic acid (Compound 40)

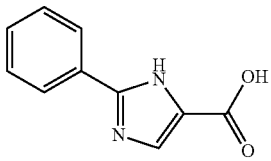 [SMILES: O=C(O)c1cnc(-c2ccccc2)[nH]1]

2.34 g (101 mmol) of sodium was dissolved in 80 ml of methanol. To this solution 1.2 g (5.6 mmol) of 2-phenyl-5-trifluoromethyl-1H-imidazole (Example 38) was added. The solution was placed in a stainless steel autoclave and was heated to 150° C. overnight. After the reaction mixture cooled to ambient temperature. It was neutralized with 10% aqueous HCl and its pH was set to 6. The solution is evaporated to dryness. The residue was extracted with chloroform and washed with water. The organic phase was dried, evaporated to dryness. Yield: 580 mg (24%).

MS (M+1): 189

TEST EXAMPLES

Test Example 1

In Vitro Pharmacological Efficacy of Compound 1 to Inhibit Different MMP Isoforms MMP activity assays were conducted as follows: MMP2, MMP9, MMP13 catalytic domain was expressed in *E. coli* in form of inclusion bodies followed by refolding and purification. The quality of the enzymes was checked using the known inhibitor ilomastat (GM6001) in the activity assay.

The Protocol of the Activity Assay:

Stock solution of substrate (Mca-Lys-Pro-Leu-Gly-Leu-Dpa-Ala-Arg-NH2) was prepared in DMSO at a concentration of 6 mM. Assays were performed in an assay buffer (50 mM Tris pH 7.5, 300 mM NaCl, 10 µM $ZnSO_4$, 5 mM $CaCl_2$, 0.005% Brij-35). The final DMSO concentration in all assays was 1.0%. The used substrate concentration was 3.33 µM. The assays were carried out at 37° C. The fluorescence changes, resulting from the substrate cleavage, were detected using excitation at 340 nm and emission wavelength of 405 nm using a Wallac 1420 Microplate Reader. The reaction mixtures were preincubated with the inhibitors for 30 minutes. The reactions were started by the addition of MMP substrate, and the fluorescence intensity changes were measured after 60 minutes. The obtained fluorescence values were normalized and % inhibition values calculated. Dose response curves were determined from 6 concentration points using three fold dilution steps, each concentration point was determined in duplicate. $IC_{50}$ values were calculated from the dose response curves. FIGS. 1-4 show the dose response curves of Compound 1 and ilomastat on on MMP1, -2, -9, -13 activities respectively. Table 1 summarizes the $IC_{50}$s determined for Compound 1 and ilomastat on MMP1, -2, -9, -13, Table 2 shows MMP inhibitions determined for other compounds described in the patent. The selectivity of the compounds on different MMP isoenyzmes can be seen in Table 1 and 2.

TABLE 1

|  | Compound 1 | ilomastat |
| --- | --- | --- |
| $IC_{50}$ on MMP1 | 51 µM | 0.5 nM |
| $IC_{50}$ on MMP2 | 5.7 µM | 1.0 nM |
| $IC_{50}$ on MMP9 | 37 µM | 0.1 nM |
| $IC_{50}$ on MMP13 | 2.5 µM | 0.2 nM |

TABLE 2

| MMP Inhibitor | MMP2 $IC_{50}$ | MMP9 $IC_{50}$ | MMP13 $IC_{50}$ | MM1 $IC_{50}$ |
| --- | --- | --- | --- | --- |
| Compound 1 | 5.7 µM | 37 µM | 2.5 µM | 51 µM |
| Compound 2 | 105 µM | 163 µM | 3.7 µM | 185 µM |
| Compound 5 | 25 µM | 9.8 µM | 4.7 µM | 6 µM |
| Compound 6 | 26 µM | 10 µM | 1.76 µM | 26 µM |
| Compound 7 | 10 µM | 13 µM | 3.2 µM | 11 µM |
| CGX (known) | 21 µM | 15 µM | 1.62 µM | 3.6 µM |
| Compound 9 | 8 µM | 8.8 µM | 1.24 µM | 47 µM |
| Compound 10 | >500 µM | >500 µM | 1.5 µM | >500 µM |
| Compound 11 | >500 µM | 140 µM | 27 µM | 280 µM |
| Compound 12 | >500 µM | >500 µM | 8.5 µM | >500 µM |
| Compound 13 | 54 µM | >500 µM | 1.5 µM | 115 µM |
| Compound 14 | 90 µM | >500 µM | 8 µM | 240 µM |
| Compound 15 | 30 µM | 20 µM | 3 µM | 17 µM |
| Compound 16 | >500 µM | 280 µM | 5 µM | 340 µM |
| Compound 17 | 195 µM | 230 µM | 19 µM | 200 µM |
| Compound 18 | >500 µM | 230 µM | 13 µM | >500 µM |
| Compound 19 | 200 µM | >500 µM | 19 µM | 190 µM |
| Compound 20 | >500 µM | >500 µM | 7.5 µM | 325 µM |
| Compound 22 | 35 µM | 8 µM | 0.28 µM | 16 µM |
| Compound 26 | >500 µM | >500 µM | 34 µM | >500 µM |
| Compound 30 | 6.6 µM | 13 µM | 1.76 µM | 3.9 µM |
| Compound 31 | >500 µM | >500 µM | 10 µM | 235 µM |
| Compound 32 | >500 µM | 200 µM | 31 µM | 90 µM |
| Compound 30 HCl | 15 µM | 100 µM | 3.3 µM | 33 µM |
| Compound 39 | >500 µM | >500 µM | 340 µM | not determined |
| Compound 40 | 137 µM | 250 µM | 165 µM | not determined |

TABLE 2-continued

| MMP Inhibitor | MMP2 IC$_{50}$ | MMP9 IC$_{50}$ | MMP13 IC$_{50}$ | MM1 IC$_{50}$ |
|---|---|---|---|---|
| Compound 35 | >500 μM | >500 μM | 500 μM | not determined |
| Compound 36 | >500 μM | >500 μM | 300 μM | not determined |
| Compound 37 | 66 μM | 145 μM | >500 μM | not determined |
| Compound 38 | 62 μM | 80 μM | 54 μM | not determined |

Test Example 2

Toxicity of Novel MMP Inhibitors

Beside the inhibitory effect on MMPs we tested the cytotoxicity of the selected compounds. These measurements were done in parallel on two cell lines. One of them was the healthy human fibroblast cell line MRC-5 while the other was the human colon tumor cell line HCT116. The viability of the cells was monitored using alamarBlue. This dye is reduced by the cells resulting in an increased fluorescent signal which is proportional to the number of living cells. Cells were incubated with the dilutions of the tested compounds for 48 hours then alamarBlue was added to them for 4 hours. After that the fluorescence changes were detected using excitation at 540 nm and emission wavelength of 590 nm by a Wallac 1420 Microplate Reader. IC$_{50}$ values were determined for the compounds using six concentrations and duplicate points for each concentration. The IC$_{50}$ values for the Compounds are summarized in Table 3 below:

TABLE 3

| Compound | MRC-5 LC$_{50}$ | HCT116 LC$_{50}$ |
|---|---|---|
| 1 | 25 μM | 11 μM |
| 2 | 0.8 μM | 0.5 μM |
| 5 | 43 μM | 3.5 μM |
| 6 | 18 μM | 3.5 μM |
| 7 | 117 μM | 73 μM |
| ALBH-known | 33 μM | 3.5 μM |
| 9 | 12 μM | 4.7 μM |
| 10 | 20 μM | 20 μM |
| 11 | 12 μM | 5.8 μM |
| 12 | 90 μM | 37 μM |
| 13 | 11 μM | 20 μM |
| 14 | 42 μM | 19 μM |
| 15 | 2.9 μM | 1.0 μM |
| 16 | 1.9 μM | 1.8 μM |
| 17 | 15 μM | 47 μM |
| 18 | 2.9 μM | 0.04 μM |
| 19 | 27 μM | 7.3 μM |
| 20 | 13 μM | 16 μM |
| 22 | 2.0 μM | 0.7 μM |
| 26 | 40 μM | 25 μM |
| 30 | 30 μM | 6 μM |
| 31 | 200 μM | 70 μM |
| 32 | 13 μM | 0.7 μM |
| 30HCl | 15 μM | 5.6 μM |

Test Example 3

In Vitro Zymography Assay to Screen the Efficacy of MMP-Inhibitiors

MMP-2 and MMP-9 enzymes were isolated from rat hearts and from rat spleen while human, recombinant MMP-1 and MMP-13 enzymes used were commercial. MMP-2, -9, -13 enzymes were separated by electrophoresis during non-reducing conditions on 8% SDS-polyacrylamide gels copolymerized with 2 mg/ml gelatin from porcine skin (Sigma Aldrich) while MMP-1 was separated under the same conditions on 8% SDS-polyacrylamide gels copolymerized with 2 mg/ml casein (Sigma Aldrich). Activation of MMP-1 proforms was achieved with trypsine. In case of MMP-13 p-aminophenylmercuric acetate (APMA) was used for enzyme activation at 37° C. for 30 min. After electrophoresis, gels were washed in 2.5% Triton-X 100 with agitation and then incubated for 20 hrs at 37° C. in enzyme incubation buffer (50 mM Tris-HCl, pH 7.5, containing 5 mM CaCl$_2$, 200 mM NaCl) with or without MMP inhibitor. Zymographic gels were stained in Coomassie Brilliant Blue R-250 and de-stained. Gelatin and casein zymograms were scanned. MMP activity is detected as a white zone on a blue background and the clear bands in the gel can be quantified by densitometry. The obtained density values were measured and % inhibition values calculated (Kupai et al., 2010). The table below summarizes the prescreen inhibition values determined for different MMP inhibitors on MMP1, -2, -9, -13.

TABLE 4

Efficacy of novel MMP inhibitors on MMP-1 isoform

| | ENZYME (kDa) | | | |
|---|---|---|---|---|
| | MMP-1 (55 kDa) | | MMP-1 (52 kDa) | |
| | Concentration | | | |
| Compound | 1 μM (% ± SD) | 100 μM (% ± SD) | 1 μM (% ± SD) | 100 μM (% ± SD) |
| Compound 30 | No inhibition | 61.06 ± 6.78 | No inhibition | 63.37 ± 18.26 |
| Compound 1 | 29.21 ± 38.74 | 95.27 ± 8.17 | 25.89 ± 9.51 | 57.98 ± 12.57 |

TABLE 5

Efficacy of novel MMP inhibitors on MMP-2 isoform

| | ENZYME (kDa) MMP-2 (72 kDa) Concentration | |
|---|---|---|
| Compound | 1 μM (% ± SD) | 100 μM (% ± SD) |
| Compound 30 | No inhibition | 100 |
| Compound 5 | No inhibition | 11.14 ± 1.58 |
| Compound 12 | 5.59 ± 11.79 | 4.78 ± 7.18 |
| Compound 14 | No nhibiton | 100 |
| Compound 1 | 100 | 100 |
| ALBH-known | No inhibition | 100 |

TABLE 6

Efficacy of novel MMP inhibitors on MMP-9 isoform

| | ENZYME (kDa) MMP-9 (92 kDa) Concentration | |
|---|---|---|
| Compound | 1 μM (% ± SD) | 100 μM (% ± SD) |
| Compound 1 | No inhibition | No inhibition |

TABLE 7

Efficacy of novel MMP inhibitors on MMP-13 isoform

| | ENZYME (kDa) MMP-13 (50 kDa) Concentration | |
|---|---|---|
| Compound | 1 μM (% ± SD) | 100 μM (% ± SD) |
| Compound 22 | No inhibition | 71.73 ± 4.49 |
| Compound 10 | No inhibition | 53.65 ± 18.89 |
| Compound 1 | 54.41 ± 2.33 | No inhibition |

TABLE 8

$IC_{50}$ values of novel MMP inhibitors on MMP-2 isoform

| Compounds | IC50 on MMP-2 (μM) |
|---|---|
| Compound 30 | 0.081 |
| Compound 1 | 11.19 |
| ILOMASTAT | 0.71 nM |

Test Example 4

Cytoprotective Effect of MMP Inhibitor Molecules in Cardiac Myocytes Subjected to Hypoxia and Reoxygenation This example shows that the presence of MMP-inhibitor during simulated ischemia and reperfusion exerts a direct cytoprotective effect in rat cardiac myocytes subjected simulated ischemia and reoxygenation.

Neonatal rat hearts were digested and isolated cardiomyocytes were plated onto 24-well plastic plates at 105 cell density. The cells were maintained at 37° C. in a humidified atmosphere of 5% $CO_2$ and 95% air in a $CO_2$ incubator until confluence was reached. Cultures at day 3 were used for treatments. Cells were kept under normoxic or simulated ischemic conditions, i.e. the growth medium was changed to a normoxic or hypoxic solution and the cells were incubated under 95% air and 5% CO2 or 95% N2 and 5% CO2 at 37° C. for 4 h, respectively as described in detail (Gorbe A, Giricz Z, Szunyog A, Csont T, Burley D S, Baxter G F, Ferdinandy P. *Role of cGMP-PKG signaling in the protection of neonatal rat cardiac myocytes subjected to simulated ischemia/reoxygenation*. Basic Res Cardiol. 105:643-650, 2010). The positive control ilomastate (0.5 microM) and MMP-inhibitors at different effective concentrations (EC 5, EC 10, EC 20, and EC50 as determined in previous test examples) were applied during normoxia or simulated ischemia and also during reoxygenation. The vehicle was DMSO. Cell viability was determined after Calcein A M fluorescent staining as described (Karliner J S, Honbo N, Summers K, Gray M O, Goetzl E J. The lysophospholipids sphingosine-1-phosphate and lysophosphatidic acid enhance survival during hypoxia in neonatal rat cardiac myocytes. *J Mol Cell Cardiol*, 33:1713-7, 2001). Total cell count was determined after digitonin treatment to permeabilize the cells by using propidium iodine fluorescent staining (Roy S S, Hajnoczky G. *Calcium, mitochondria and apoptosis studied by fluorescence measurements*. Methods. 46:213-223, 2008).

MMP inhibitor compounds exerted a dose-dependent direct cytoprotective effect in cardiac myocytes (Table 9). The positive control ilomastat exterted an approximately 120% cytoprotective effect as compared to vehicle-treated cells.

TABLE 9

Cytoprotective effect of MMP inhibitors at EC5, EC10, EC20, and EC50 concentrations.

| Test Compound | EC5 | EC10 | EC20 | EC50 |
|---|---|---|---|---|
| Compound 1 | 2.6 microM | 6.3 microM | 10.4 microM | 17.7 microM |
| normoxia | 120 ± 2* | 99 ± 2 | 94 ± 2 | 86 ± 2# |
| simulated ischemia | 125 ± 6* | 109 ± 2 | 106 ± 2 | 97 ± 2 |
| Compound 8 | 0.7 microM | 2.0 microM | 6.0 microM | 18.0 microM |
| normoxia | 99 ± 4 | 103 ± 4 | 119 ± 5* | 127 ± 4* |
| simulated ischemia | 117 ± 12 | 120 ± 8 | 144 ± 25 | 107 ± 8 |
| Compound 10 | 0.3 microM | 1.0 microM | 3.0 microM | 9.0 microM |
| normoxia | 112 ± 3* | 112 ± 1* | 115 ± 3* | 108 ± 1 |
| simulated ischemia | 117 ± 2* | 119 ± 2* | 123 ± 6* | 136 ± 2* |

TABLE 9-continued

Cytoprotective effect of MMP inhibitors at
EC5, EC10, EC20, and EC50 concentrations.

| Test Compound | EC5 | EC10 | EC20 | EC50 |
|---|---|---|---|---|
| Compound 15 | 3.0 microM | 10.0 microM | 30.0 microM | 90.0 microM |
| normoxia | 95 ± 2 | 99 ± 2 | 100 ± 2 | 83 ± 2# |
| simulated ischemia | 109 ± 5 | 117 ± 5* | 114 ± 4* | 88 ± 4 |
| Compound 16 | 4.0 microM | 8.0 microM | 16.0 microM | 32.0 microM |
| normoxia | 105 ± 2 | 108 ± 3* | 99 ± 2 | 91 ± 2# |
| simulated ischemia | 119 ± 3* | 119 ± 3* | 122 ± 4* | 113 ± 4* |
| Compound 31 | 0.3 microM | 0.6 microM | 1.2 microM | 2.5 microM |
| normoxia | 97 ± 4 | 102 ± 5 | 104 ± 3 | 105 ± 4 |
| simulated ischemia | 109 ± 5 | 103 ± 4 | 111 ± 4 | 147 ± 2* |
| Compound 31 HCl | 0.25 microM | 1.0 microM | 4.0 microM | 16.0 microM |
| normoxia | 108 ± 4 | 103 ± 3 | 106 ± 4 | 103 ± 3 |
| simulated ischemia | 116 ± 8* | 107 ± 3 | 126 ± 2* | 127 ± 3* |

Cytoprotective effect is expressed as % cell survival as compared to vehicle DMSO.
*$p < 0.05$ shows significantly increased cell survival (i.e. cytoprotection).
$p < 0.05$ shows significantly decreased cell survival.

Test Example 5

Effect of Compound 1 on Myocardial
Ischemia/Reperfusion Injury in Rat Hearts

This example shows that the presence of MMP-inhibitor administered before ischemia and during reperfusion modifies infarct size and influences the ischemia/reperfusion injury in isolated rat hearts.

Figure 6:
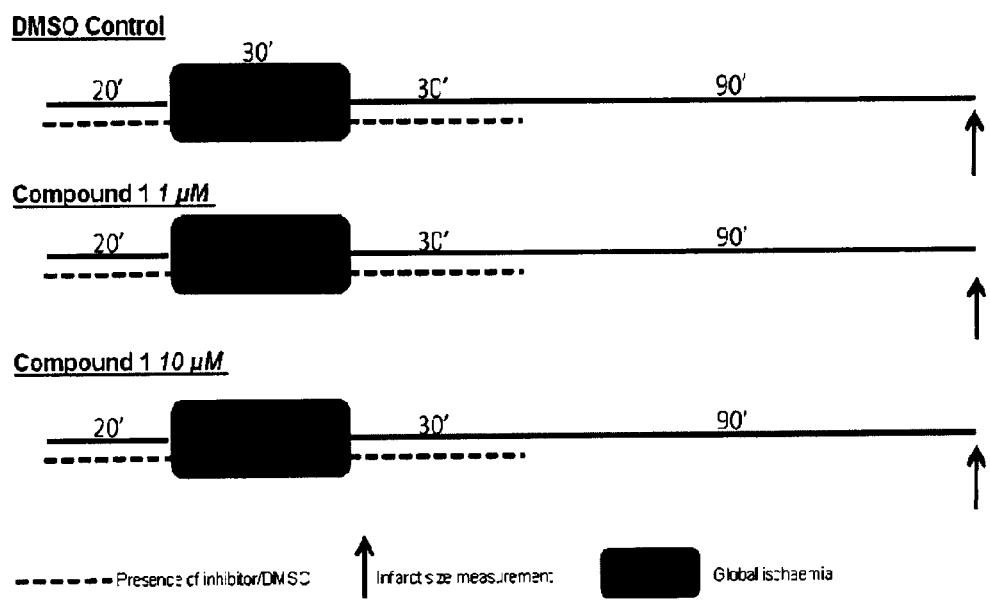
FIG. 6. Experimental protocol. Control and inhibitor treated hearts were subjected to 20 min stabilization followed by 30 min global ischemia and 120 min reperfusion.

Male Wistar rats were anesthetized with diethyl ether, heparin (500 U/kg i.v.) was administered and hearts were isolated. The hearts were assigned to three groups: (i) DMSO control and (ii) Compound 1 (1 µM) and (iii) Compound 1 (10 µM) treated. Stock solution of inhibitors was prepared in DMSO. The final DMSO concentration in all assays was 0.1%. Hearts were perfused in Langendorff mode with constant pressure (100 H$_2$O cm) for 20 min at 37° C. then exposed to global ischemia for 30 min followed by 120 min of reperfusion. The DMSO and inhibitors were dissolved in Krebs-Henseleit buffer and administered only before onset of ischemia for 20 min (pretreatment) and during the first 30 min of reperfusion (FIG. 6). At the end of reperfusion, infarct size (IS) was defined by triphenyltetrazolium chloride staining (Csonka et al., 2010).

In separate experiments hearts were perfused to test cardioprotective effect of ALBH-know compound at 5 µM final concentration. The same protocol was used as mentioned above. ALBH-know compound was able to reduce myocardial IS by 72.01±4.96% as compared to vehicle.

Figure 7:
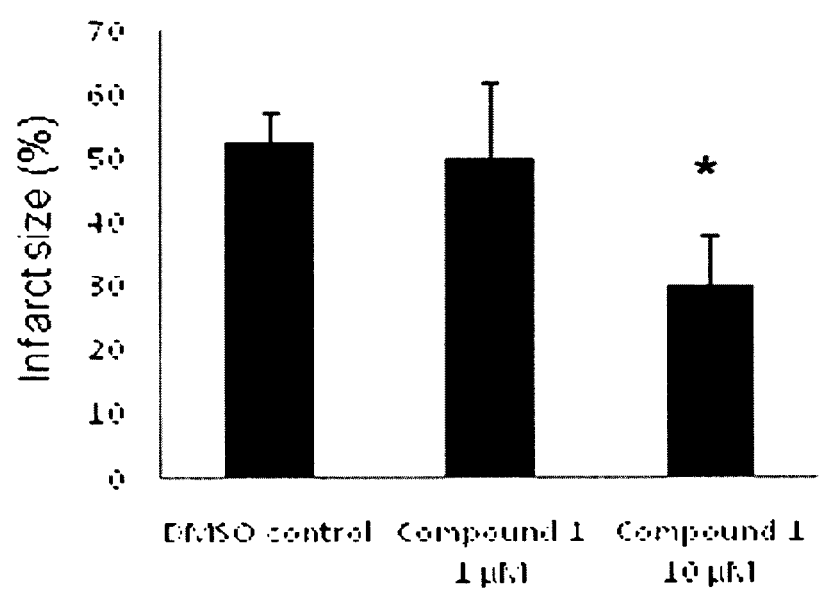
FIG. 7. Infarct size. Compound 1 (10 µM) significantly decreased infarct size as compared with DMSO control. (n=4-9; p<0.05, T-test).

The Compound 1 or DMSO administered before ischemia and during reperfusion reduced myocardial IS (FIG. 7) in dose dependant way. These findings may identify new potential therapeutics that prevent MMP release after ischemia and resulting in a significant reduction in cardiac ischemia/reperfusion injury and protect against acute myocardial infarction.

In summary, the novel compounds and ALBH-known compound presented above show significantly more selectivity in the inhibition of different MMP isoenzymes as compared to the selectivity of the reference compound ilomastat. Compound 1 for example is highly selective for MMP2, while it spares MMP9, and show moderate inhibition on MMP1 and MMP13. Compound 1, which is selective for MMP2, decreased infarct size significantly. Although the potency of MMP inhibition of the novel compounds and ALBH-known compound are less than the reference compound ilomastat, but according the current literature, moderate inhibition of certain MMPs are sufficient to treat some pathologies, e.g. acute myocardial infarction by only a 20% inhibition of MMP2 as described in reference 15 below.

REFERENCE LIST

1. Ahokas, K, Lohi, J, Lohi, H, Elomaa, O, Karjalainen-Lindsberg, M L, Kere, J & Saarialho-Kere, U. (2002). Matrix metalloproteinase-21, the human orthologue for XMMP, is expressed during fetal development and in cancer. *Gene*, 301, 31-41.
2. Csonka, C, Csont, T, Onody, A & Ferdinandy, P. (2001). Preconditioning decreases ischemia/reperfusion-induced peroxynitrite formation. *Biochem Biophys Res Commun*, 285, 1217-1219.
3. Csonka, C, Kupai, K, Kocsis, G F, Novak, G, Fekete, V, Bencsik, P, Csont, T & Ferdinandy, P. (2010). Measurement of myocardial infarct size in preclinical studies. *J Pharmacol Toxicol Methods*, 61, 163-170.
4. Davis, G E & Saunders, W B. (2006). Molecular balance of capillary tube formation versus regression in wound repair: role of matrix metalloproteinases and their inhibitors. *J Investig Dermatol Symp Proc*, 11, 44-56.
5. Do, H & Nataatmadja, M.
6. Dorman, G, Cseh, S, Hajdu, I, Barna, L, Konya, D, Kupai, K, Kovacs, L & Ferdinandy, P. (2010). Matrix metalloproteinase inhibitors: a critical appraisal of design principles and proposed therapeutic utility. *Drugs*, 70, 949-964.
7. Dorman, G, Kocsis-Szommer, K, Spadoni, C & Ferdinandy, P. (2007). MMP inhibitors in cardiac diseases: an update. *Recent Pat Cardiovasc Drug Discov*, 2, 186-194.
8. Fang, Y J, Pan, Z Z, Li, L R, Lu, Z H, Zhang, L Y & Wan, D S. (2009). MMP7 expression regulated by endocrine therapy in ERbeta-positive colon cancer cells. *J Exp Clin Cancer Res*, 28:132, 132.
9. Fernandez-Patron, C, Radomski, M W & Davidge, S T. (1999). Vascular matrix metalloproteinase-2 cleaves big endothelin-1 yielding a novel vasoconstrictor. *Circ Res*, 85, 906-911.
10. Fernandez-Patron, C, Stewart, K G, Zhang, Y, Koivunen, E, Radomski, M W & Davidge, S T. (2000a). Vascular matrix metalloproteinase-2-dependent cleavage of calcitonin gene-related peptide promotes vasoconstriction. *Circ Res*, 87, 670-676.

11. Fernandez-Patron, C, Stewart, K G, Zhang, Y, Koivunen, E, Radomski, M W & Davidge, S T. (2000b). Vascular matrix metalloproteinase-2-dependent cleavage of calcitonin gene-related peptide promotes vasoconstriction. *Circ Res,* 87, 670-676.
12. Fingleton, B. (2007). Matrix metalloproteinases as valid clinical targets. *Curr Pharm Des,* 13, 333-346.
13. Folgueras, A R, Valdes-Sanchez, T, Llano, E, Menendez, L, Baamonde, A, Denlinger, B L, Belmonte, C, Juarez, L, Lastra, A, Garcia-Suarez, O, Astudillo, A, Kirstein, M, Pendas, A M, Farinas, I & Lopez-Otin, C. (2009). Metalloproteinase MT5-MMP is an essential modulator of neuro-immune interactions in thermal pain stimulation. *Proc Natl Acad Sci USA,* 106, 16451-16456.
14. Gao, C Q, Sawicki, G, Suarez-Pinzon, W L, Csont, T, Wozniak, M, Ferdinandy, P & Schulz, R. (2003). Matrix metalloproteinase-2 mediates cytokine-induced myocardial contractile dysfunction. *Cardiovasc Res,* 57, 426-433.
15. Giricz, Z, Lalu, M M, Csonka, C, Bencsik, P, Schulz, R & Ferdinandy, P. (2006). Hyperlipidemia attenuates the infarct size-limiting effect of ischemic preconditioning: role of matrix metalloproteinase-2 inhibition. *J Pharmacol Exp Ther,* 316, 154-161.
16. Grossetete, M, Phelps, J, Arko, L, Yonas, H & Rosenberg, G A. (2009). Elevation of matrix metalloproteinases 3 and 9 in cerebrospinal fluid and blood in patients with severe traumatic brain injury. *Neurosurgery,* 65, 702-708.
17. Hegedus, L, Cho, H, Xie, X & Eliceiri, G L. (2008). Additional MDA-MB-231 breast cancer cell matrix metalloproteinases promote invasiveness. *J Cell Physiol,* 216, 480-485.
18. Hernandez-Barrantes, S, Bernardo, M, Toth, M & Fridman, R. (2002). Regulation of membrane type-matrix metalloproteinases. *Semin Cancer Biol,* 12, 131-138.
19. Kitaoka, H, Kubo, T, Okawa, M, Hayato, K, Yamasaki, N, Matsumura, Y & Doi, Y L. (2010). Impact of metalloproteinases on left ventricular remodeling and heart failure events in patients with hypertrophic cardiomyopathy. *Circ J,* 74, 1191-1196.
20. Kuivanen, T, Ahokas, K, Virolainen, S, Jahkola, T, Holtta, E, Saksela, O & Saarialho-Kere, U. (2005). MMP-21 is upregulated at early stages of melanoma progression but disappears with more aggressive phenotype. *Virchows Arch,* 447, 954-960.
21. Kupai, K, Szucs, G, Cseh, S, Hajdu, I, Csonka, C, Csont, T & Ferdinandy, P. (2010). Matrix metalloproteinase activity assays: Importance of zymography. *J Pharmacol Toxicol Methods,* 61, 205-209.
22. Lagente, V, Le Quement, C & Boichot, E. (2009). Macrophage metalloelastase (MMP-12) as a target for inflammatory respiratory diseases. *Expert Opin Ther Targets,* 13, 287-295.
23. Lang, R, Braun, M, Sounni, N E, Noel, A, Frankenne, F, Foidart, J M, Bode, W & Maskos, K. (2004). Crystal structure of the catalytic domain of MMP-16/MT3-MMP: characterization of MT-MMP specific features. *J Mol Biol,* 336, 213-225.
24. Lehrke, M, Greif, M, Broedl, U C, Lebherz, C, Laubender, R P, Becker, A, von Ziegler, F, Tittus, J, Reiser, M, Becker, C, Goke, B, Steinbeck, G, Leber, A W & Parhofer, K G. (2009). MMP-1 serum levels predict coronary atherosclerosis in humans. *Cardiovasc Diabetol,* 8:50, 50.
25. Li, L, Mei, T H, Zhou, X D & Zhang, X G. (2009). Expression and clinical significance of matrix metalloproteinase (MMP)-26 protein in non-small cell lung cancer. *Chin J Cancer,* 28, 60-63.
26. Lin, Y H, Lin, L Y, Wu, Y W, Chien, K L, Lee, C M, Hsu, R B, Chao, C L, Wang, S S, Hsein, Y C, Liao, L C, Ho, Y L & Chen, M F. (2009). The relationship between serum galectin-3 and serum markers of cardiac extracellular matrix turnover in heart failure patients. *Clin Chim Acta,* 409, 96-99.
27. Lindsey, M L. (2004). MMP induction and inhibition in myocardial infarction. *Heart Fail Rev,* 9, 7-19.
28. Llano, E, Pendas, A M, Freije, J P, Nakano, A, Knauper, V, Murphy, G & Lopez-Otin, C. (1999). Identification and characterization of human MT5-MMP, a new membrane-bound activator of progelatinase a overexpressed in brain tumors. *Cancer Res,* 59, 2570-2576.
29. Matsumoto, Y, Park, I K & Kohyama, K. (2009). Matrix metalloproteinase (MMP)-9, but not MMP-2, is involved in the development and progression of C protein-induced myocarditis and subsequent dilated cardiomyopathy. *J Immunol,* 183, 4773-4781.
30. Matziari, M, Dive, V & Yiotakis, A. (2007). Matrix metalloproteinase 11 (MMP-11; stromelysin-3) and synthetic inhibitors. *Med Res Rev,* 27, 528-552.
31. McClain, J A, Phillips, L L & Fillmore, H L. (2009). Increased MMP-3 and CTGF expression during lipopolysaccharide-induced dopaminergic neurodegeneration. *Neurosci Lett,* 460, 27-31.
32. Momiyama, Y, Ohmori, R, Tanaka, N, Kato, R, Taniguchi, H, Adachi, T, Nakamura, H & Ohsuzu, F. (2009). High plasma levels of matrix metalloproteinase-8 in patients with unstable angina. *Atherosclerosis.*
33. Polewicz, D, Cadete, V J, Doroszko, A, Hunter, B E, Sawicka, J, Szczesna-Cordary, D, Light, P E & Sawicki, G. (2010). Ischemia induced peroxynitrite dependent modifications of cardiomyocyte MLC1 increases its degradation by MMP-2 leading to contractile dysfunction. *J Cell Mol Med.*
34. Schulz, R. (2007). Intracellular targets of matrix metalloproteinase-2 in cardiac disease: rationale and therapeutic approaches. *Annu Rev Pharmacol Toxicol,* 47:211-42., 211-242.
35. Sedlacek, R, Mauch, S, Kolb, B, Schatzlein, C, Eibel, H, Peter, H H, Schmitt, J & Krawinkel, U. (1998). Matrix metalloproteinase MMP-19 (RASI-1) is expressed on the surface of activated peripheral blood mononuclear cells and is detected as an autoantigen in rheumatoid arthritis. *Immunobiology,* 198, 408-423.
36. Selvey, S, Haupt, L M, Thompson, E W, Matthaei, K I, Irving, M G & Griffiths, L R. (2004). Stimulation of MMP-11 (stromelysin-3) expression in mouse fibroblasts by cytokines, collagen and co-culture with human breast cancer cell lines. *BMC Cancer,* 4:40, 40.
37. Shah, V K, Shalia, K K, Mashru, M R, Soneji, S L, Abraham, A, Kudalkar, K V, Vasvani, J B & Sanghavi, S T. (2009). Role of matrix metalloproteinases in coronary artery disease. *Indian Heart J,* 61, 44-50.
38. Spinale, F G. (2007). Myocardial matrix remodeling and the matrix metalloproteinases: influence on cardiac form and function. *Physiol Rev,* 87, 1285-1342.
39. Stephanopoulos, G, Garefalaki, M E & Lyroudia, K. (2005). Genes and related proteins involved in amelogenesis imperfecta. *J Dent Res,* 84, 1117-1126.
40. Sung, M M, Schulz, C G, Wang, W, Sawicki, G, Bautista-Lopez, N L & Schulz, R. (2007). Matrix metalloproteinase-2 degrades the cytoskeletal protein alpha-actinin in peroxynitrite mediated myocardial injury. *J Mol Cell Cardiol,* 43, 429-436.
41. Thiolloy, S, Halpern, J, Holt, G E, Schwartz, H S, Mundy, G R, Matrisian, L M & Lynch, C C. (2009).

Osteoclast-derived matrix metalloproteinase-7, but not matrix metalloproteinase-9, contributes to tumor-induced osteolysis. *Cancer Res,* 69, 6747-6755.

42. Vaalamo, M, Kariniemi, A L, Shapiro, S D & Saarialho-Kere, U. (1999). Enhanced expression of human metalloelastase (MMP-12) in cutaneous granulomas and macrophage migration. *J Invest Dermatol,* 112, 499-505.
43. Wang, W, Schulze, C J, Suarez-Pinzon, W L, Dyck, J R, Sawicki, G & Schulz, R. (2002). Intracellular action of matrix metalloproteinase-2 accounts for acute myocardial ischemia and reperfusion injury. *Circulation,* 106, 1543-1549.
44. Woessner, J F, Jr. (2002). MMPs and TIMPs—an historical perspective. *Mol Biotechnol,* 22, 33-49.
45. Yoshida, W, Uzuki, M, Nishida, J, Shimamura, T & Sawai, T. (2009). Examination of in vivo gelatinolytic activity in rheumatoid arthritis synovial tissue using newly developed in situ zymography and image analyzer. *Clin Exp Rheumatol,* 27, 587-593.
46. Zhang, B, Cao, X, Liu, Y, Cao, W, Zhang, F, Zhang, S, Li, H, Ning, L, Fu, L, Niu, Y, Niu, R, Sun, B & Hao, X. (2008). Tumor-derived matrix metalloproteinase-13 (MMP-13) correlates with poor prognoses of invasive breast cancer. *BMC Cancer,* 8:83, 83.
47. Zhang, K, McQuibban, G A, Silva, C, Butler, G S, Johnston, J B, Holden, J, Clark-Lewis, I, Overall, C M & Power, C. (2003). HIV-induced metalloproteinase processing of the chemokine stromal cell derived factor-1 causes neurodegeneration. *Nat Neurosci,* 6, 1064-1071.
48. Zhang, X, Zhu, S, Luo, G, Zheng, L, Wei, J, Zhu, J, Mu, Q & Xu, N. (2007). Expression of MMP-10 in lung cancer. *Anticancer Res,* 27, 2791-2795.

The invention claimed is:
1. Compounds, or salts or solvates thereof, of general formula:

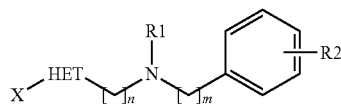

wherein
n is 1, 2 or 3,
m is 1, 2 or 3,
HET is an optionally substituted 5 to 6-membered heteroaromatic group comprising 3 to 5 carbon atoms and 1 to 2 heteroatoms independently selected from the group consisting of N, O and S;
X is $CF_3$, halogen, COOR3 or CONHR3, wherein R3 is H or $C_{1-6}$ alkyl;
R1 is $(CH_2)_o$-aryl, $(CH_2)_p$-heteroaryl, $(CH_2)_q$-biphenyl, wherein o, p and q is 1, 2 or 3, or $C_{1-6}$ alkyl which is optionally substituted with 1 or 2 aryl group(s);
  C(O)—R5, where R5 is aryl or heteroaryl, optionally substituted with halogen;
  $S(O)_2$—R6, where R6 is aryl or heteroaryl, optionally substituted with halogen;
R2 is H, Y—$(CH_2)_r$-aryl, Y—$(CH_2)_s$-heteroaryl, wherein r and s is 1, 2 or 3, S—($C_{1-6}$ alkyl) which is optionally substituted with 1 or 2 aryl group(s) or O—($C_{1-6}$ alkyl) which is substituted with 1 or 2 aryl group(s);
Y is O or S;
wherein in the meaning of X, R1 and R2 each instance of alkyl is optionally substituted with 1-3 substituent(s) independently selected from the group of halogen, alkoxy, hydroxyl, carboxyl, $CF_3$, nitro, sulphate, amino, monoalkylamino, dialkylamino and cyano;
wherein in the meaning of R1 and R2 each instance of aryl, heteroaryl and biphenyl is optionally substituted with 1-3 substituent(s) independently selected from the group of halogen, alkyl, alkoxy, hydroxyl, carboxyl, $CF_3$, nitro, sulphate, amino, monoalkylamino, dialkylamino and cyano;
with the exclusion of the compound where HET is 1,3-thiazol, X is COOH, R1 is 4-fluorophenyl and R2 is benzyloxy.
2. A compound or salts or solvates thereof according to claim 1, wherein
  X is $CF_3$ or COOR3, wherein R3 is H or optionally substituted $C_{1-4}$ alkyl.
3. A compound or salts or solvates thereof according to claim 1, wherein R1 is selected from the group of $CH_2$-aryl, $CH_2$-heteroaryl, $CH_2$-biphenyl or $CH_2$—$CH_2$-biphenyl, diphenyl-methyl, 2,2'-diphenyl-ethyl, 3,3'-diphenyl-propyl, C(O)—R5, where R5 is aryl and $S(O)_2$—R6, where R6 is aryl, where each of the said groups is optionally substituted with halogen in the aromatic part.
4. A compound or salts or solvates thereof according to claim 1, wherein R2 is selected from the group of O—$CH_2$-aryl, O—$CH_2$-heteroaryl, O—($C_{1-6}$ alkyl) which is optionally substituted with 1 or 2 aryl group(s), where each of the said groups is optionally substituted with halogen in the aromatic part.
5. A compound or salts or solvates thereof according to claim 1, wherein Y is O.
6. A compound or salts or solvates thereof according to claim 1, wherein
  HET is 5-membered heteroaromatic group comprising 1 to 2 heteroatoms independently selected from the group consisting of N, O and S;
  X is $CF_3$ or COOR1, wherein R1 is H or $C_{1-3}$ alkyl;
  R1 is $CH_2$-aryl, $CH_2$-heteroaryl, $CH_2$-biphenyl or 2,2'-diphenyl-ethyl, where each of the said groups is optionally substituted with halogen in the aromatic part;
  R2 is O—$CH_2$-aryl, O—$CH_2$-heteroaryl, diphenylmethoxy, where each of the said groups is optionally substituted with halogen in the aromatic part.
7. A compound or salts or solvates thereof according to claim 1, wherein
  HET is

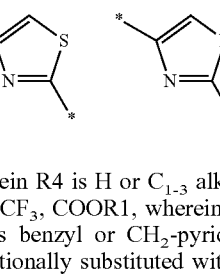

wherein R4 is H or $C_{1-3}$ alkyl;
  X is $CF_3$, COOR1, wherein R1 is H or methyl or ethyl;
  R1 is benzyl or $CH_2$-pyridinyl, where the groups are optionally substituted with fluorine,
  R2 is O-benzyl or O—$CH_2$-pyridinyl, where the groups are optionally substituted with fluorine.
8. Pharmaceutical composition comprising a compound according to claim 1 together with one or more usual pharmaceutical auxiliary material(s).
9. A compound or salts or solvates thereof according to claim 2, wherein R3 is optionally substituted methyl or ethyl.
10. A compound or salts or solvates thereof according to claim 1, wherein R2 is O—($CH_2$)-aryl optionally substituted with halogen, O—(CH$_2$)-heteroaryl optionally substituted with halogen, or O—(C$_{1-6}$ alkyl) which is substituted with 1 or 2 aryl group(s) and optionally substituted with halogen.

11. A compound or salts or solvates thereof according to claim 10, wherein the O—(C$_{1-6}$ alkyl) is substituted with a diphenylmethoxy group.

12. A compound or salts or solvates thereof according to claim 1, wherein R2 is O—(CH$_2$)-pyridinyl optionally substituted with halogen.

13. A compound or salts or solvates thereof according to claim 1, wherein R2 is H, Y—(CH$_2$)$_r$-aryl, Y—(CH$_2$)$_s$-heteroaryl, wherein r and s is 1, 2 or 3, or S—(C$_{1-6}$ alkyl) which is optionally substituted with 1 or 2 aryl group(s).

14. A compound or salts or solvates thereof of general formula:

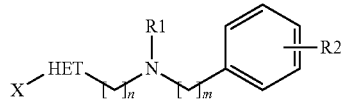

wherein
n is 1, 2 or 3,
m is 1, 2 or 3,
HET is an optionally substituted 5 to 6-membered heteroaromatic group comprising 3 to 5 carbon atoms and 1 to 2 heteroatoms independently selected from the group consisting of N, O and S;

X is CF$_3$, halogen, COOR3 or CONHR3, wherein R3 is H or C$_{1-6}$ alkyl;

R1 is (CH$_2$)$_o$-aryl, (CH$_2$)$_p$-heteroaryl, (CH$_2$)$_p$-biphenyl, wherein o, p and q is 1, 2 or 3, or C$_{1-6}$ alkyl which is optionally substituted with 1 or 2 aryl group(s);
  C(O)—R5, where R5 is aryl or heteroaryl, optionally substituted with halogen;
  S(O)$_2$—R6, where R6 is aryl or heteroaryl, optionally substituted with halogen;

R2 is selected from the group consisting of O—CH$_2$-aryl, O—CH$_2$-heteroaryl and O—(C$_{1-6}$ alkyl) which is optionally substituted with 1 or 2 aryl group(s), where each of the said groups is optionally substituted with halogen in the aromatic part;

wherein in the meaning of X and R1 each instance of alkyl is optionally substituted with 1-3 substituent(s) independently selected from the group of halogen, alkoxy, hydroxyl, carboxyl, CF$_3$, nitro, sulphate, amino, monoalkylamino, dialkylamino and cyano;

wherein in the meaning of R1 each instance of aryl, heteroaryl and biphenyl is optionally substituted with 1-3 substituent(s) independently selected from the group of halogen, alkyl, alkoxy, hydroxyl, carboxyl, CF$_3$, nitro, sulphate, amino, monoalkylamino, dialkylamino and cyano;

with the exclusion of the compound where HET is 1,3-thiazol, X is COOH, R1 is 4-fluorophenyl and R2 is benzyloxy.

* * * * *